US006428579B1

(12) United States Patent
Valentini

(10) Patent No.: US 6,428,579 B1
(45) Date of Patent: Aug. 6, 2002

(54) IMPLANTABLE PROSTHETIC DEVICES COATED WITH BIOACTIVE MOLECULES

(75) Inventor: Robert F. Valentini, Cranston, RI (US)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 09/446,942

(22) PCT Filed: Jul. 1, 1998

(86) PCT No.: PCT/US98/13792

§ 371 (c)(1),
(2), (4) Date: May 12, 2000

(87) PCT Pub. No.: WO99/01089

PCT Pub. Date: Jan. 14, 1999

(51) Int. Cl.[7] .................................................. A61F 2/36
(52) U.S. Cl. ................................. 623/23.76; 623/23.74; 427/2.13; 427/2.24; 606/76
(58) Field of Search .......................... 623/23.76, 23.74, 623/23.57, 23.51, 23.6; 427/2.1, 2.31

(56) References Cited

U.S. PATENT DOCUMENTS

| | | | | | |
|---|---|---|---|---|---|
| 4,181,757 A | * | 1/1980 | Youdelis | ...................... | 427/2.1 |
| 4,263,681 A | * | 4/1981 | Notton | ......................... | 3/1.91 |
| 4,578,079 A | | 3/1986 | Ruoslahti et al. | | |

(List continued on next page.)

FOREIGN PATENT DOCUMENTS

WO          89/05150 A1      6/1989

OTHER PUBLICATIONS

Lodish Berk Zipursky Matsudaira Baltimore Darnell—"Molecular Cell Biology" Fourth Edition pp. 988–989, 1993.*
Bain, C.D. et al., "Formation of Monolayers by the Coadsorption of Thiols on Gold: Variation in the Length of the Alkyl Chain", *J. Am. Chem. Soc.*, 1989, pp. 7164–7175, vol. 111, No. 18, American Chemical Society.

Laibinis, P.E. et al., "Orthogonal Self–Assembled Monolayers: Alkanethiols on Gold and Alkane Carboxylic Acids on Alumina", *Science*, Aug. 25, 1989, pp. 845–847, vol. 245.
Moodie, G. et al., "Immobilization of Bioactive Peptides to Metal Surfaces", *Official Journal for Artificial Organs and the International Faculty for Artificial Organs*, Jun. 1997, Abstract #80, p. 494, vol. 21, No. 6.
Pierce Chemical Corp. Catalog, pp. 104, 105 and 110, Listing SPDP, SATA and Trauts Reagent.
Pytela, R. et al., "Arginine–Glycine–Aspartic Acid Adhesion Receptors", *Methods in Enzymology*, 1987, pp. 475–489, vol. 144, Academic Press, Inc.
Sasaki, Y.C. et al., "Two–Dimensional Arrangement of a Functional Protein by Cysteine–Gold Interaction: Enzyme Activity and Characterization of a Protein Monolayer on a Gold Substrate", *Biophysical Journal*, Apr. 1997, pp. 1842–1848, vol. 72, Biophysical Society.
Whitesides, G.M. et al., "Wet Chemical Approaches to the Characterization of Organic Surfaces: Self–Assembled Monolayers, Wetting, and the Physical–Organic Chemistry of the Solid–Liquid Interface", *The Langmuir Lectures*, 1990, pp. 87–96, vol. 6, No. 1.

*Primary Examiner*—David H. Willse
*Assistant Examiner*—Suzette J. Jackson
(74) *Attorney, Agent, or Firm*—Wolf, Greenfield & Sacks, P.C.

(57) ABSTRACT

Coated implantable prosthetic devices are disclosed. The device is a prosthetic having a gold layer on the surface to which bioactive molecules are attached through a gold-sulfhydryl bond. The devices are easy and convenient to prepare. Gold coated implantable devices are also disclosed herein. The gold coated implantable device is a prosthetic device formed of a porous non-fabric material having a surface with projections and indentations and the gold layer on the surface of the porous non-fabric material forms a uniform layer across the material such that the gold layer also forms projections and indentations.

39 Claims, 2 Drawing Sheets

U.S. PATENT DOCUMENTS

| | | | |
|---|---|---|---|
| 4,614,517 A | | 9/1986 | Ruoslahti et al. |
| 4,756,711 A | * | 7/1988 | Mai et al. ................. 623/23.15 |
| 4,822,369 A | * | 4/1989 | Oueveau et al. ......... 623/22.21 |
| 4,871,366 A | | 10/1989 | von Recum et al. |
| 4,879,237 A | | 11/1989 | Rudslahti et al. |
| 4,960,423 A | * | 10/1990 | Smith ........................ 623/1.48 |
| 4,988,621 A | | 1/1991 | Ruoslahti et al. |
| 5,041,380 A | | 8/1991 | Ruoslahti et al. |
| 5,092,885 A | | 3/1992 | Yamada et al. |
| 5,120,829 A | * | 6/1992 | Pierschbacher et al. ..... 530/326 |
| 5,207,706 A | | 5/1993 | Menaker |
| 5,225,064 A | | 7/1993 | Henkens et al. |
| 5,278,063 A | | 1/1994 | Hubbell et al. |
| 5,330,911 A | | 7/1994 | Hubbell et al. |
| 5,344,654 A | | 9/1994 | Rueger et al. |
| 5,384,073 A | | 1/1995 | Shigekawa et al. |
| 5,464,438 A | | 11/1995 | Menaker |
| 5,468,562 A | | 11/1995 | Farivar et al. |
| 5,607,442 A | | 3/1997 | Fischell et al. |
| 5,620,850 A | | 4/1997 | Bamdad et al. |
| 5,759,205 A | | 6/1998 | Valentini |
| 5,789,433 A | * | 8/1998 | Chan et al. .................. 514/410 |
| 5,888,067 A | * | 3/1999 | Gibbs et al. ................. 433/173 |
| 6,008,431 A | * | 12/1999 | Caldarise et al. ........ 623/16.11 |
| 6,096,726 A | * | 8/2000 | Opolski ........................ 514/53 |
| 6,131,580 A | * | 10/2000 | Ratner et al. ................ 128/898 |

* cited by examiner

IMPLANTABLE PROSTHETIC DEVICES COATED WITH BIOACTIVE MOLECULES

BACKGROUND OF THE INVENTION

Implantable prosthetic devices have been used in the surgical repair or replacement of internal tissue for many years. The efficacy of many types of implants is primarily dependent upon the surrounding tissue's adaptive reformation around and ability to bond to the implant surface. In orthopedic implants in particular, the geometry and the quality of bone reformation determines how much load the bone can resist. Orthopedic implants include a wide variety of devices, each suited to fulfill particular medical needs. Examples of such devices are hip joint replacement devices, knee joint replacement devices, shoulder joint replacement devices, and pins, braces and plates used to set fractured bones. Some contemporary orthopedic implants, including hip and knee components, use high performance metals such as cobalt-chrome and titanium alloy to achieve high strength. These materials are readily fabricated into the complex shapes typical of these devices using mature metal working techniques including casting and machining.

At least two other methods are currently employed for bone and joint replacement and repair. Those methods include: (1) the use of grouting materials such as poly (methyl methacrylate) (PMMA) as bone cement between the bone and the prosthesis; and (2) direct opposition of bone tissue onto porous and non-porous implant surfaces. The latter method is known as the "cementless implant method."

In one example of the cementless implant method, a prosthesis is coated with hydroxyapatite which is a major inorganic component of bone. The hydroxyapatite-coated prosthesis is then implanted in the bone cavity. The hydroxyapatite, which is a calcium salt, is believed to facilitate osteointegration with the bone tissues. After partial integration of the hydroxyapatite-coated prosthesis with the bone, layers of hydroxyapatite can be detected between the prosthesis and the bone tissues.

Despite the success of both metal and non-metal components in many patients, long term data has demonstrated an unacceptably high failure rate in more active patients due to loosening of the implant caused by bone resorption around the implant or failure to achieve bone ingrowth. Bone resorption results from stress shielding of the bone around the implant. The failure to achieve bone ingrowth into the surface of the implant to support implant mechanical stability has been a major problem with conventional implants. The metal orthopaedic prostheses rely on poly(methyl methacrylate) for attachment and fixation to bone. Loosening of such implants as a result of cement failure has resulted in additional surgeries for securing the implants. In order to avoid the problems associated with these prostheses, prostheses having porous or centered coatings have also been used. Although these materials encourage tissue ingrowth, the process of ingrowth occurs over a period of weeks to months, during which time the implant may be loosened and fail to function properly.

SUMMARY OF THE INVENTION

It has been discovered according to the present invention that conventional implants can be improved by coating with a layer of gold and attaching to the gold a bioactive molecule. The bioactive molecule functions at the implant surface to promote a favorable, local, environmental response. Accordingly, the invention is an improved implantable prosthetic device coated with a bioactive molecule.

The prosthetic device provided according to the invention is convenient and simple to prepare. The bioactive molecules are directly coupled to the prosthetic device surface through a gold-sulfide bond using simple solution chemistry techniques. Prior art methods for modifying the surface of biomaterials were complex and cumbersome. For instance, in order to conjugate a molecule to a polymeric surface, the surface would first have to be modified to add a functional group to which the molecule could bind. In some cases the molecule would require the addition of a linking group which is capable of reacting with the functional group.

According to one aspect, the invention is a prosthetic device including a shaped substrate having a substrate surface, for implantation in a mammal, a layer of gold attached to the substrate surface and defining a tissue contacting surface, and a bioactive molecule bound to the gold layer. The shaped substrate can be, for example, a polymer, a metal, a plastic, a fabric, a ceramic, a biological material, or a composite of two or more materials. The gold layer may be any thickness but preferably the gold layer has a thickness of about 10 to 1000 Angstroms. The bioactive molecule in turn can form a monolayer on the surface of the gold which, depending on the size of the bioactive molecule, is about 1 to 500 Angstroms in thickness.

The bioactive molecule can be virtually any molecule which can be attached to the gold layer and which can affect favorably the implant in its local environment once implanted. The bioactive molecule, therefore, can be natural or synthetic including a protein, a peptide, a protein analog, a sugar, a lipid, a glycol protein, a glycolipid or a nucleic acid. In one embodiment the bioactive molecule is selected from the group consisting of a cell modulating molecule, a chemotactic molecule, an anticoagulant moleucle, an anti-thrombotic molecule, an anti-tumor molecule, an anti-infectious molecule, a growth potentiating molecule, and an anti-inflammatory molecule. In one embodiment the cell modulating molecule is selected from the group consisting of an anti-integrin antibody, a bone morphogenic protein, an integrin binding protein, and a cadherin binding protein. In another embodiment the chemotactic molecule is an extracellular matrix molecule selected from the group consisting of collagen, fibronectin, laminin, and proetoglycan. In yet another embodiment the anti-tumor molecule is selected from the group consisting of methotrexate, adriamycin, cyclophosphamide, and taxol. The anti-infectious molecule is selected from the group consisting of antibiotics such as penicillin according to another embodiment. In another embodiment the growth potentiating molecule is selected from the group consisting of growth factors such as PDGF, EGF, FGF, TGF, NGF, CNTF, and GDNF. According to another embodiment the anti-inflammatory molecule is selected from the group consisting of steroidal and non-steroidal compounds.

The layer of gold can be attached directly to the substrate surface. In another embodiment the layer of gold is attached to the substrate surface via attachment to an intermediate layer, such as a layer of titanium intermediate the gold layer and the substrate surface.

According to another embodiment the surface of the prosthetic device is formed of a porous material, wherein the layer of gold creates a gold surface that has projections and indentations and wherein the layer of gold has an approximately uniform thickness across the surface of the porous material.

According to another aspect, the invention is a prosthetic device including a shaped substrate having a substrate surface, for implantation in a mammal, a layer of gold attached to the substrate surface and defining a tissue contacting surface, and a bioactive peptide bound to the gold layer. The shaped substrate can be, for example, a polymer, a metal, a plastic, a fabric, a ceramic, a biological material, or a composite of two or more materials. The gold layer may be any thickness but preferably the gold layer has a thickness of about 10 to 1000 Angstroms. The bioactive peptide forms a monolayer on the surface of the gold which, depending on the size of the peptide, is about 1 to 500 Angstroms in thickness.

The bioactive peptide can be any peptide which can be attached to the gold layer and which can affect favorably the implant in its local environment. It can be natural or synthetic. In one embodiment the bioactive peptide is selected from the group consisting of a cell modulating peptide, a chemotactic peptide, an anticoagulant peptide, an antithrombotic peptide, an anti-tumor peptide, an anti-infectious peptide, a growth potentiating peptide, and an anti-inflammatory peptide. In one embodiment the cell modulating peptide is selected from the group consisting of an anti-integrin antibody fragment, a cadherin binding peptide, a bone morphogenic protein fragment, and an integrin binding peptide. Preferably the cell modulating peptide is a integrin binding peptide which is selected from the group consisting of RGDC, RGEC, RGDT, DGEA, DGEAGC, EPRGDNYR, RGDS, EILDV, REDV, YIGSR, SIKVAV, RGD, RGDV, HRNRKGV, KKGHV, XPQPNPSPASPVVVGGGASLPEFXY, and ASPVVVGG-GASLPEFX. The peptides also may be any functionally active fragment of the proteins disclosed herein as being bioactive molecules useful according to the invention. In another embodiment the chemotactic peptide is selected from the group consisting of functionally active fragments of collagen, fibronectin, laminin, and proteoglycan. In yet another embodiment the anti-tumor peptide is selected from the group consisting of functionally active fragments of protein anti-tumor agents. The anti-infectious peptide is selected from the group consisting of functionally active fragments of the protein anti-infectious agents according to another embodiment. In another embodiment the growth potentiating peptide is selected from the group consisting of functionally active fragments of PDGF, EGF, FGF, TGF, NGF, CNTF, GDNF, and type I collagen related peptides. According to another embodiment the anti-inflammatory peptide is selected from the group consisting of functionally active fragments of anti-inflammatory agents.

The layer of gold can be attached directly to the substrate surface. In another embodiment the layer of gold is attached to the substrate surface via attachment to an intermediate layer, such as a layer of titanium intermediate the gold layer and the substrate surface.

According to another embodiment the surface of the prosthetic device is formed of a porous material, wherein the layer of gold creates a gold surface that has projections and indentations and wherein the layer of gold has an approximately uniform thickness across the surface of the porous material.

The invention in another aspect is a prosthetic device including a shaped substrate formed of a textured material having a substrate surface with first projections and first indentations and a layer of gold attached to the substrate surface of the textured material, wherein the layer of gold creates a gold surface that has second projections and second indentations corresponding to the first projections and first indentations. In one embodiment, the layer of gold has an approximately uniform thickness across the substrate surface of the textured material. Preferably the textured material is a porous material such as a porous titanium material, a porous polymer, or any other non-fabric porous material.

In one embodiment the textured material is a polymer. In another embodiment the gold layer has a thickness of about 10 to 1000 Angstroms.

According to yet another embodiment the prosthetic device also includes a layer of bioactive peptide attached to the gold surface through a gold-sulfide bond.

In another aspect the invention is a prosthetic device including a shaped substrate having a substrate surface, a layer of gold attached to the substrate surface, and an RGDC peptide attached to the gold layer through a gold-sulfide bond. According to an embodiment the shaped substrate is a polymer, a metal, a plastic, a fabric, a ceramic, a biological material, or a composite of two or more materials. In one embodiment the gold layer has a thickness of about 10 to 1000 Angstroms. In another embodiment the bioactive peptide forms a layer about 1 to 500 Angstroms in thickness.

The layer of gold is attached directly to the substrate surface in one embodiment. In another embodiment the layer of gold is attached to the substrate surface via attachment to a layer of titanium intermediate the gold layer and the substrate surface.

According to another embodiment the surface of the prosthetic device is formed of a porous material, wherein the layer of gold creates a gold surface that has projections and indentations. In one embodiment the layer of gold has an approximately uniform thickness across the surface of the porous material.

DETAILED DESCRIPTION OF THE INVENTION

Figure 1:
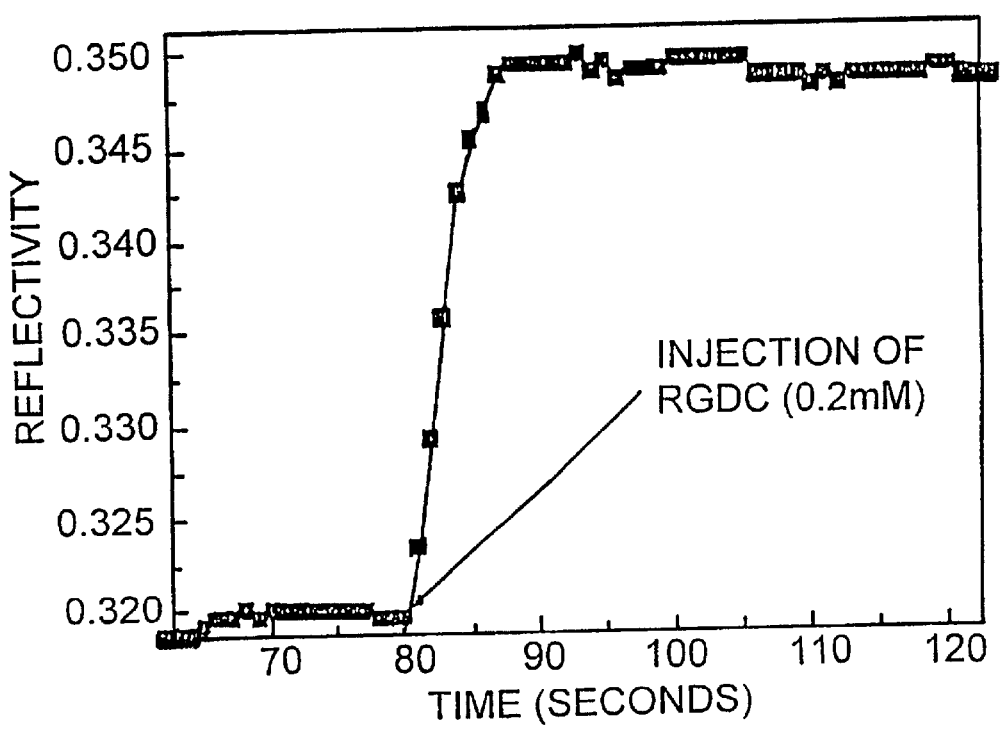
FIG. 1 is a graph depicting the observed reflectivity change upon incubation of a clean gold surface with a 0.2 mM solution of the RGDC peptide.

According to the present invention, it was discovered that an implantable device could be coated with a bioactive molecule by first coating a substrate with a gold layer and then attaching the bioactive molecule through a simple reaction to the gold layer by forming a gold-sulfide bond. Prior art methods for attaching molecules to the surface of materials are cumbersome. In order to make a polymeric or other non-metal prosthetic device coated with molecules using these prior art methods the surface of the prosthetic device would have to be modified and would most likely require the addition of coupling reagents, making the preparation of such devices expensive, time consuming, and impractical. The preparation of metal implants having molecules attached to surfaces of the implants has been a difficult challenge in the prior art because most metal surfaces have oxide layers which make binding of coupling agents difficult. The implantable prosthetic device coated with bioactive molecules disclosed herein is prepared by a simple technique for coupling bioactive molecules to biomaterial surfaces.

The function performed by the surface is defined in part by the type of bioactive molecule bound to the surface. As used herein a "bioactive molecule" is any biologically active molecule which includes a sulfhydryl group or to which a sulfhydryl group can be attached directly or indirectly. Examples are a peptide, protein (e.g., apoprotein, glycoprotein, antigen and antibody), a protein analog containing at least one non-peptide linkage in place of a peptide linkage, a nucleic acid, etc. Nucleic acids include nucleotides; oligonucleotides; and their art-recognized and biologically functional analogs and derivatives including, for example, oligonucleotide analogs having phosphorothioate linkages.

Preferred bioactive molecules include a cell modulating molecule, a chemotactic molecule, anticoagulant moleucle, antithrombotic molecule, an anti-tumor molecule, an anti-infectious molecule, a growth potentiating molecule, and an anti-inflammatory molecule.

A cell modulating molecule as used herein is a molecule that interacts with a cell and modifies the cell in any way e.g. alters gene expression, such as bone morphogenic protein, anti-integrin antibodies, integrin binding protein, and cadherin binding protein.

A chemotactic molecule as used herein is a molecule which attracts cells to a surface or aids in a cell's attachment to a surface and includes extracellular matrix proteins such as collagen, fibronectin, laminin, and proetoglycan.

An anti-tumor molecule as used herein is a molecule which decreases or prevents a further increase in growth of a tumor and includes anti-cancer agents such as Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride, and Taxol.

An anti-infectious molecule as used herein is a molecule which reduces the activity of or kills a microorganism and includes Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Ornidazole; Pentisomicin; and Sarafloxacin Hydrochloride.

A growth potentiating molecule as used herein is a molecule which stimulates growth of a cell and includes growth factors such as PDGF, EGF, FGF, TGF, NGF, CNTF, and GDNF.

An anti-inflammatory molecule as used herein is a molecule which reduces an inflammatory response and includes steroidal and non-steroidal compounds; Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; s Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

An anticoagulant moleucle as used herien is a molceule that prevents clotting of blood and includes but is not limited to Ancrod; Anticoagulant Citrate Dextrose Solution; Anticoagulant Citrate Phosphate Dextrose Adenine Solution; Anticoagulant Citrate Phosphate Dextrose Solution; Anticoagulant Heparin Solution; Anticoagulant Sodium Citrate Solution; Ardeparin Sodium; Bivalirudin; Bromindione; Dalteparin Sodium; Desirudin; Dicumarol; Heparin Calcium; Heparin Sodium; Lyapolate Sodium; Nafamostat Mesylate; Phenprocoumon; Tinzaparin Sodium; Warfarin Sodium.

An antithrombotic moleucle as used herien is a molceule that prevents formation of a thrombus and includes but is not limited to Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; Trifenagrel.

Preferably the bioactive molecule is a bioactive peptide. A "bioactive peptide" as used herein refers to oligopeptides having a chain of less than or equal to fifty amino acids and which is capable of performing a desired biological function. In a preferred embodiment the bioactive molecule includes a cell modulating peptide, a chemotactic peptide, an anticoagulant peptide, an antithrombotic peptide, an anti-tumor peptide, an anti-infectious peptide, a growth potentiating peptide, and an anti-inflammatory peptide. A cell modulating peptide includes, for example, an antibody fragment or an integrin binding peptide. Bioactive peptides include peptide fragments of the proteins which are bioactive molecules disclosed herein and having the functional properties of those proteins.

A preferred use for the peptide-coated implantable device of the invention is for enhancing and/or accelerating bone growth in areas of damaged bone or in bone replacement surgery. Bone and joint replacement surgeries are commonly used, for instance, to relieve pain, improve function, and enhance the quality of life for patients with medical conditions caused by osteoarthritis, rheumatoid arthritis, post-traumatic degeneration, avascular necrosis, and other aging-related conditions. The prosthetic device of the invention which is coated with bioactive peptides that enhance or accelerate bone growth significantly improve the ability of an implant to remain attached to the bone surface. Preferred integrin binding peptides which perform this function are RGDC, RGEC, RGDT, DGEA, DGEAGC, EPRGDNYR, RGDS, EILDV, REDV, YIGSR, SIKVAV, RGD, RGDV, and HRNRKGV.

Anti-infectious peptides include include antibiotic peptides such as those disclosed in U.S. Pat. No. 5,602,097. Anti-tumor and anti-infectious peptides are also disclosed in U.S. Pat. No. 5,516,755. U.S. Pat. No. 5,484,885 discloses chemotactic, antibiotic, and lipopolysaccharide binding peptide fragments of CAP37 protein. These peptide sequences are approximately five consecutive amino acids long. U.S. Pat. No. 5,354,736 discloses several collagen type I related peptides which are useful for promoting growth.

Growth potentiating peptides also include low molecular weight tibial growth potentiating peptides such as those disclosed in U.S. Pat. No. 5,576,301. These peptides are useful for potentiating tibial growth. These peptides have the following sequences: XPQPNPSPASPVVVGG-GASLPEFXY and ASPVVVGGGASLPEFX.

Bioactive peptides such as those disclosed above are well known in the art. Other bioactive peptides useful according to the invention may be identified through the use of synthetic peptide combinatorial libraries such as those disclosed in Houghton et al., *Biotechniques*, 13(3):412–421 (1992) and Houghton et al., *Nature*, 354:84–86 (1991) or using phage display procedures such as those described in Hart, et al., *J. Biol. Chem.* 269:12468 (1994). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Ligands that bind selectively to a specific molecule such as a cell surface receptor are obtained by selecting those phages which express on their surface a ligand that binds to the specific molecule. Ligands that possess a desired biological activity can be screened in known biological activity assays and selected on that basis. These phages then are subjected to several cycles of reselection to identify the peptide-expressing phages that have the most useful characteristics. Typically, phages that exhibit the binding characteristics (e.g., highest binding affinity or cell stimulatory activity) are further characterized by nucleic acid analysis to identify the particular amino acid sequences of the peptides expressed on the phage surface and the optimum length of the expressed peptide to achieve optimum biological activity. Alternatively, such peptides can be selected from combinatorial libraries of peptides containing one or more amino acids. Such libraries can further be synthesized which contain non-peptide synthetic moieties which are less subject to enzymatic degradation compared to their naturally-occurring counterparts. U.S. Pat. No. 5,591,646 discloses methods and apparatuses for biomolecular libraries which are useful for screening and identifying bioactive peptides. Methods for screening peptides libraries are also disclosed in U.S. Pat. No. 5,565,325.

Peptides obtained from combinatorial libraries or other sources can be screened for functional activity by methods known in the art. For instance when the peptide is a cell modulating peptide, and in particular an integrin binding peptide, one of ordinary skill in the art can easily determine whether the peptide will modulate bone cell activity by performing the in vitro studies set forth in example 2 to measure osteoblast differentiation. Likewise, similar experiments can be conducted for other types of cells using cell specific markers of differentiation or growth. The type of assay of course, used for a particular peptide depends on the source of the peptide. For instance if a peptide is a fragment of an anti-tumor molecule, the peptide should be tested for functional activity in an anti-tumor assay. Those of skill in the art can easily choose an appropriate assay for testing functionality of a particular peptide.

The bioactive molecules useful according to the invention are commercially available from many sources and methods for making these molecules also are well known in the art. Bioactive peptides and proteins may easily be synthesized or produced by recombinant means. Such methods are well known to those of ordinary skill in the art. Peptides and proteins can be synthesized for example, using automated peptide synthesizers which are commercially available. Alternatively the peptides and proteins can be produced by recombinant techniques by incorporating the DNA expressing the peptide into an expression vector and transforming cells with the expression vector to produce the peptide.

The bioactive molecule is bound to a gold surface. Although many attempts have been made in the prior art to coat peptides, proteins and other biomaterials on various surfaces, each of these techniques has required the use of complex coupling techniques and surface modification including the use of coupling agents and linkers. It has been discovered according to the present invention that bioactive molecules can be attached to a prosthetic device via a gold surface, through a simple technique that results in the formation of a bond between a gold and a sulfhydryl group. The bond that forms between a sulfhydryl group and gold only requires the interaction between the sulfhydryl group and the gold in a solution. The interaction does not require coupling agents or linkers or surface activation or modification of the gold.

The molecule is added to the gold surface using simple solution chemistry techniques, e.g., simply exposing the gold surface to a solution of molecule in a solvent such as ethanol:water. This approach is simple and is non-line of sight dependent. A technique which is line of sight dependent only coats an external surface and does not coat internal pores or interstices. Non-line of sight dependent methods are capable of coating the internal surface area such as pores. This technique produces an evenly coated layer of molecule on any type of device, even those having a porous, spongy, or textured surface.

Bioactive molecules can be attached to gold surfaces directly or via spacers. If direct, then bioactive molecules must have (or must be modified to have) a sulfhydryl group. If indirect, the bioactive molecule may or may not have sulfhydryl, but the spacer will have a sulfhydryl. In this instance the spacer is attached to the gold surface and the bioactive molecule is attached to the spacer, before or after attaching the spacer to the gold surface. Proteins or peptides having endogenous cysteine groups already have a cysteine within the molecule and do not require the addition of another sulfhydryl group. If a protein or peptide has more than one cysteine and those cysteines have formed di-sulfide bridges the molecule can be subjected to reducing agents to ensure that the sulfhydryl group is free and available.

Proteins or peptides without endogenous cysteine groups can easily be manipulated to incorporate a sulfhydryl group. For instance, peptides and proteins can be subjected to site directed mutagenesis to prepare a cysteine containing protein or peptide. Additionally a cysteine can be added to either the N-terminal or C-terminal of the peptide or protein or incorporated within the peptide or protein or within a branch of the peptide or protein. A cysteine may be added anywhere in the peptide or protein that does not affect the biological activity of the peptide or protein. This is demonstrated schematically as follows:

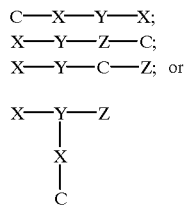

wherein X, Y, and Z are any amino acid and C is cysteine. Preferably a cysteine group is added to either the C-terminal or the N-terminal of the peptide. More preferably, the cysteine group is on the C terminal region of the peptide.

Proteins or peptides without endogenous cysteine and other non-sulfhydryl containing molecules can easily be manipulated to incorporate a non-cysteine sulfhydryl group. For example, sulfhydryl groups can be introduced into the molecules having a primary amine (or modified to have a primary amine) by reaction of the primary amine in the molecule with 2-iminothiolane or Traut's reagent, or other commercially available reagents. A variety of commercially available reagents for coupling sulfhydryl groups to molecules are available from Pierce Chemical, Corp., such as Traut's reagent (Product No. 26101), SATA (Product No. 26102) or SPDP (Products Nos. 21757, 21657, 21557). Traut's reagent is a water soluble reagent which reacts with primary amines at pH 7–10 to introduce sulfhydryl groups, as disclosed in Schram and Dulffer, *Physiol. Chem.,* 358, 137–139 (1977). Traut's reagent has the following structure:

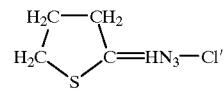

SATA is a reagent which adds protected sulfhydryls to molecules by reacting with primary amines. SATA has the following chemical structure:

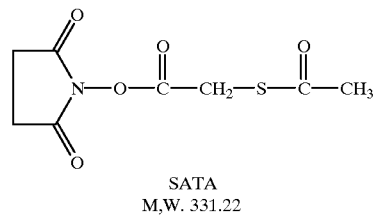

SATA
M,W. 331.22

SPDP, which includes LC-SPDP and Sulfo-LC-SPDP also is capable of adding a sulfhydryl group to primary amines. These molecules have the following structures:

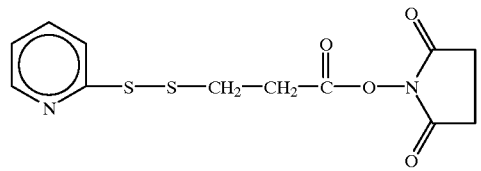

SPDP
M,W, 312.4
UNCLEAR

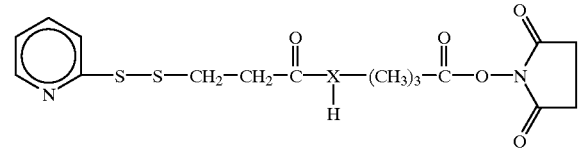

LC-SPDP

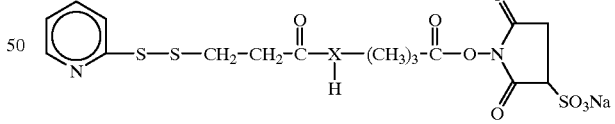

Sullo-LC-SPDP

Preferably, the bioactive molecule is prepared with a sulfhydryl group at, for example, the carboxyl (C) or amino (N) terminus and then is coupled to the gold surface. In an alternative embodiment, a spacer is synthesized with a sulfhydryl group, preferably at or near one end, and then this spacer is attached at this end to the gold surface and via a different functional group to the bioactive molecule. The spacer molecule may be coupled for example to the terminal amine group or carboxyl group of the bioactive peptide or protein. Spacer molecules can be selected, for example, which contain (or which can be modified to contain) a functional group that is reactive with the peptide or protein N-terminal amine group and allowing the functional group and the peptide or protein N-terminal amine to form a linkage in accordance with art-recognized procedures. See, e.g., March, J., *Advanced Organic Chemistry,* 4th Ed., New York, N.Y., Wiley and Sons, 1985), pp.326–1120. In an analogous manner, the spacer molecule may be coupled to a reactive group in the C-terminus of the bioactive peptide or protein. Additionally the spacer molecule may be coupled to a branch of a molecule or an internally active portion of a molecule or any end group.

Thiol or amide groups may be added at any nucleotide of a nucleic acid. The amine group may be added so as to provide a point of attachment for a sulfhydryl group by the above-described reagents. Nucleic acids may also be synthesized with groups such as amine groups.

The bioactive molecule is bound to a layer of gold which is attached to a substrate surface of a shaped substrate. The layer of gold covers all or part of the prosthetic device to define a tissue contacting surface. The tissue contacting surface is the surface of the gold to which the molecules are bound. The layer of gold may be extremely thin or it may be thick. The layer of gold may actually be the entire prosthetic device. In this case the layer of gold would encompass the shaped substrate as well. Preferably the layer of gold is thin because of the high cost of gold.

The layer of gold is attached to the shaped substrate surface by any means known in the art. For instance, the gold layer can be added to the implant using evaporation, electroplating, sputtering or electrodeposition. Using any of these techniques the gold can be applied in a thin layer to the surface of the implant. Preferably the gold is attached to the substrate by electroplating or evaporation. Electroplating produces a gold layer which is non-line of site dependent. Using electroplating, therefore, a gold layer can be produced on an uneven surface such that the uneven nature of the surface is maintained.

A shaped substrate as used herein is a material which has the shape of an implantable prosthetic. The selection of the shape of the prosthetic is governed by the physical requirements of space, geometry and function at the region where the implant is to be positioned in the body. Implants can be made available in a range of sizes to fit the varying sizes in the patient population.

In some embodiments, the bioactive molecule coating is on and within the pores of an implantable prosthesis of the type where tissue ingrowth is contemplated, wherein the bioactive molecule encourages the ingrowth of the tissue into the pores or facilitates attachment of tissue to the prosthetic. In another embodiment, the coating is on a typical prosthesis or on a 'temporary implant', such as a long term but temporary catheter, and the coating is of an antibacterial agent to prevent colonization upon the prosthesis or catheter. Thus, the invention is useful in connection with prosthetic devices such as bone or joint replacement or repair prosthetics, vascular prostheses, including woven prostheses, catheters for implantation and the like. Virtually any implantable tissue contacting surface may be modified as described herein.

The shaped substrate may be made from any material ordinarily used to prepare implants. For instance the shaped substrate may be made from any of a wide variety of metals, such as, pure titanium, titanium alloy, stainless steel, cobalt-chrome alloy, and gold. The shaped substrate may also be made from polymeric matrix composites, such as continuous filament carbon, graphite, glass and aramid fibers embedded within a polymer matrix, such as polysulfone, polyether-ether-ketone, polyether-ketone-ketone, polyimide, epoxy or polycyanate, polymers including polyethylene, polyetheretherketone (PEEK), polypropylene, polymethylmethacrylate, polyamides, and polyester. Other polymeric matrix composites include but are not limited to polyethylene films, ultra-high molecular weight polyethylene films and fibers, polyvinylidene fluoride films, poly (methyl methacrylate) films, polystyrene films, nylon 12 films and fibers, various polyesters and polyacrylates, polyetherethereketones, aromatic polyamides, polyethylene terephthalate fibers and films, poly(tetramethylene terephthalate) films, and polyether-esters of poly (tetramethylene terephthalate).

The prosthetic device of the invention is useful for implantation in mammals. Mammals herein means humans, cats, dogs, mice, hamsters, pigs, goats, primates, horses, cows, and sheep.

A preferred prosthetic device of the invention is a shaped substrate having a substrate surface, a layer of gold attached to the substrate surface, and an RGDC peptide attached to the gold layer through a gold-sulfide bond. The RGD peptide is a peptide found in many extracellular matrix proteins which is known to bind $\alpha_5\beta_1$ and $\alpha_v\beta_3$ integrin receptors. RGD attached to surfaces has been demonstrated to increase osteoblast attachment to the surface. It is preferred that orthopedic prosthetic devices are coated with RGDC.

The prosthetic device with the bioactive molecule attached to the surface has been found to be extremely stable and as a result can be stored for extended periods of time. The stability of the device is important because it enables the device to be prepared in advance and shipped to a medical institution where it can be stored for future implantation. As a result medical institutions can store many prosthetic devices having various molecules already coated on the surface for various applications.

The prosthetic device of the invention may also be prepared and stored without the bioactive molecule attached to the device. The bioactive molecule can then be added at a later time point prior to use. The step of adding the bioactive molecule to the gold surface is simple and quick and may easily be performed immediately prior to a surgical process. Accordingly, the prosthetic device of the invention also includes a shaped substrate formed of a textured material and having a gold layer attached to the surface. More specifically the shaped substrate has a substrate surface with first projections and first indentations and a layer of gold is attached to the substrate surface of the textured material such that the layer of gold creates a gold surface that has second projections and second indentations corresponding to the first projections and indentations. The layer of gold optionally has an approximately uniform thickness across the substrate surface of the textured material.

A "textured material" as used herein is a non-fabric material having small (about 1–1000 microns in size) interstices throughout. The shaped substrate may be made entirely of a textured material or may optionally be made of a non-textured material but having a surface which is coated with a textured material to produce a textured surface. Preferably the textured material is a porous material such as a porous titanium material, a porous polymer, or any other non-fabric porous material. Porous metal surfaces have been created by plasma spraying (U.S. Pat. No. 3,605,123) of fine metallic particles, or by sintering a loosely packed coating of metallic particles (U.S. Pat. No. 4,550,448, British Patent No. 1,316,809), or by diffusion bonding kinked fiber metal pads (U.S. Pat. No. 3,906,550). Plasma spraying employs super heated gases to melt the metal particles to be sprayed. Sintering develops interparticle bonds in a porous coating by exposing the coating and implant metal to temperatures approaching their melting point, while diffusion bonding employs heat and pressure to promote atomic diffusion at the coating implant interface. Methods for preparing porous polymer materials are well known in the art. Additionally the shaped substrate may be made of a non-textured material but having a surface which is at least partially coated with a textured material to produce a partially textured surface. Thus the invention also encompasses a prosthetic device having a shaped substrate made from a non-textured material but at least partially coated with a textured material on which a layer of gold is attached.

The substrate surface of the textured material has projections and indentations. "Projections and indentations" as used herein are microscopic cavities on the surface of the substrate defining a 'rough' surface microscopically. A substrate surface is said to have projections and indentations if it has a substantial region that is mostly free of a flat smooth surface, but instead is characterized by numerous indentations and projections throughout the region, numerous cavities having a diameter between 1 micron and 1 millimeter, preferably between 20 microns and 900 microns. In a preferred embodiment the gold layer attached to the textured material creates a gold surface that also has projections and indentations and that has an approximately uniform thickness across the substrate surface.

The following examples are provided to illustrate the methods and products of the present invention. As described above, many variations on these particular examples are possible and, therefore, the examples are merely illustrative and not limiting of the present invention. As demonstrated in the Examples below the implantable prosthetic device of the invention has many advantages over uncoated implants and even over peptide-coated implants that do not have a gold surface.

EXAMPLES

The following examples describe experiments which were conducted on molecule-coated gold surfaces. Experiments were also carried out on molecule coated polymer surfaces (FEP) which serve as controls. By comparing the results obtained with the gold-coated substrate with those obtained with the FEP material it is possible to distinguish the effects which occur as a result of the immobilized peptide from those which occur as a result of the surface context of the immobilized peptide.

Example 1

Immobilization of Peptides on Biomaterial Surfaces

Methods and Materials

Peptides: The peptides used in the following studies are set forth in Table I. All peptides were synthesized commercially (QCB, Hopkinton, Mass.) to a purity of 98% or greater by HPLC and mass spectrometry. Peptides being coupled to FEP (the control substrate) included G or GGGG spacer sequence on their N- or C-terminus. Peptides being coupled to gold coated surfaces included a CG or CGGG spacer sequence on their N- or C-terminus. Control peptides were fabricated using scrambled sequences or, if known, amino acid substitutions.

TABLE 1

| Extracellular Matrix Protein | Peptide Ligand | Integrin Receptors |
|---|---|---|
| Collagen I | cRGD, RGDT, DGEA | $\alpha_1\beta_1, \alpha_2\beta_1, \alpha_3\beta_1$ |
| Bone Sialoprotein | EPRGDNYR | $\alpha_v\beta_3$ |
| Osteopontin | RGD | $\alpha_v\beta_3$ |
| Fibronectin | RGDS, EILDV, REDV | $\alpha_3\beta_1, \alpha_4\beta_1, \alpha_5\beta_1, \alpha_v\beta_1, \alpha_v\beta_3, \alpha_v\beta_5, \alpha_v\beta_6, \alpha_4\beta_7$ |
| laminin | YIGSR, SIKVAV, RGD | $\alpha_1\beta_1, \alpha_2\beta_1, \alpha_3\beta_1, \alpha_6\beta_1, \alpha_7\beta_1, \alpha_6\beta_4$ |
| Thrombospondin | RGD | $\alpha_v\beta_3$ |
| Vitronectin | RGDV, HRNRKGV | $\alpha_v\beta_1, \alpha_v\beta_3, \alpha_v\beta_5$ |
| Osteonectin (SPARC) | KKGHK | ? |

Human and rat osteoblast/osteocytes express a range of integrins. These are shown in Table 2 below.

TABLE 2

| Rat Calvarial Osteoblasts | $\alpha_1\beta_1, \alpha_5\beta_1, \alpha_v\beta_1, \alpha_v\beta_3, \alpha_v\beta_5$ |
|---|---|
| Human Osteoblasts | $\alpha_3\beta_1, \alpha_4\beta_1, \alpha_5\beta_1, \alpha_v\beta_3$ |

Preparation of Gold Coated Substrates 12-mm diameter pre-cleaned circular glass cover slips were obtained from Fisher Scientific and placed into a custom mount consisting of a 0.25 inch thick aluminum plate. The samples were then suspended inside a four-source NRC 3177 electron beam evaporator with a Sloan 180° electron gun and Sloan Six/Ten power supply. The gold coating did not adhere well to plain glass, so titanium was used as an intermediate. The evaporator chamber was pumped down to achieve a vacuum in the low $10^{-6}$ to high $10^{-7}$ torr range. Initial pumping was done with a mechanical pump and then a diffusion pump was brought on line to achieve and maintain the final pressure. A liquid nitrogen trap was employed to keep the system free of contaminating vapors from diffusion pump oil or other contaminants. The electron beam gun was activated and a 60 angstrom coating of Ti was put onto the cover slips. The Ti source was then rotated away as the gold source was rotated into place. A 500 angstrom layer of gold was applied. The samples were then removed from the system and kept under nitrogen or covered in Kimwipes and aluminum foil until ready for use.

Immobilization of peptides on Gold Coated Substrates

Cysteine terminated peptides were solubilized in a 1:1 ethanol:distilled water solution at a concentration of 0.22 mM. The gold substrates were exposed to this solution for one hour. Plain gold controls were made by exposing samples to peptide-free ethanol:distilled water for one hour. Reactions were carried out in the dark to protect the light-sensitive cysteine.

Preparation of FEP Membranes with Immobilized Peptide

FEP membranes with immobilized peptide are useful for comparison purposes. The FEP membranes were prepared using surface modification and coupling techniques. FEP films (Dupont) 25 micrometers thick were cut into discs with a lathe (1.76 cm diameters) and cleaned by sonication in hexanes and methanol for 20 seconds each. Surface hydroxyl (OH) groups were added to cleaned FEP films by a radio frequency glow discharge (RFGD) process. The films were placed in a chamber and brought to a pressure of 100 millitorr. The chamber was filled with hydrogen and methanol vapor at 500 millitorr for 10 minutes. The pressure was again reduced to 100 millitorr and the radio frequency glow discharge was activated for 1 minute.

After rinsing the hydroxylated REP films in DMSO, the films were reacted with CDI (40 mg/1 ml in DMSO) for 24 hours. To enhance nucleophilic attack of the OH— group to the CDI substrate, the solution was supplemented with N-Hydroxy-succinimide (NHS, Fluka) (1 mg/ml in DMSO) (Frost, 1981) The excess CDI/NHS was rinsed off of the films with DMSO before applying the peptide solution. Films were placed in 0.22 M peptide in 1M MES buffer (pH 5) for 48 hours (Hearn, 1987). Films were rinsed sequentially with 1M MES buffer, 1M NaCl, and distilled water. This stringent rinsing protocol was used to remove adsorbed vs. linked peptide from the surface.

The chemical reactions for the CDI Activation and the peptide coupling reactions are as follows:

CDI Activation

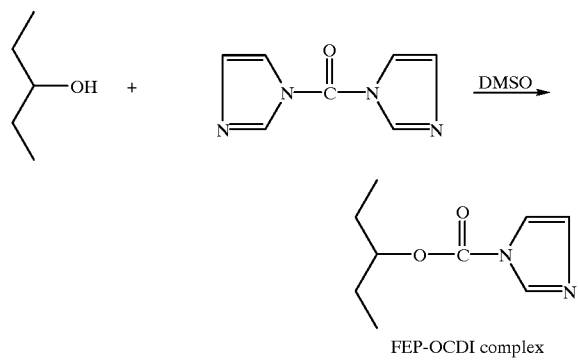

FEP-OCDI complex

Peptide Coupling:

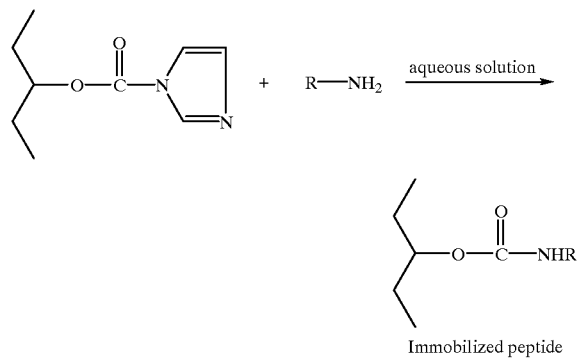

Immobilized peptide

The scheme for FEP and gold coated substrates are shown below.

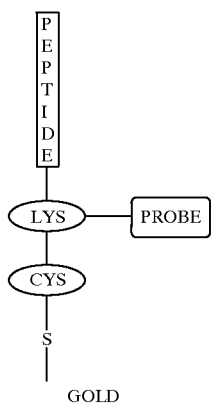

GOLD

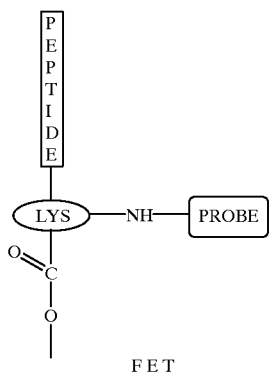

FET

Methods for Surface Characterization

1. Contact Angle

Contact angles were measured with ethylene glycol, glycerol, distilled water, and ethanol on a goniometer. Each fluid was placed on the substrate using a syringe with a 30 gauge needle. At least three measurements per drop were taken. The surface energy was calculated using E. Sacher's method (Ratner, 1988; Kaelble, 1974; Kaelble, 1970). Contact angle data provides information regarding the surface chemistry and surface energetics of the top 5 Angstroms of a polymer substrate. A bead of pure liquid with a known surface tension is placed on the polymer surface. The resulting bead angle is measured using a goniometer (an alternate technique is to use a Cahn microbalance). A hydrophobic surface causes liquid beading and a high contact angle while a more hydrophilic surface is wettable and a small contact angle is observed. A range of fluids with polar (i.e. water) to non-polar (i.e. decane) characteristics are tested.

2. Surface-Plasmon Resonance

Surface plasmon resonance (SPR) was produced when a beam of p-polarized laser light impinges onto the surface of a thin metal film. The light was coupled to the metal film through a prism which was mounted on a rotating turntable. At a particular angle of incidence the E-field of the laser light interacts with the surface bound free electrons of the metal film in such a way that a charge density wave was generated at the interface of the metal and air. This excitation results in a sharp reduction in the magnitude of the reflected light (measured with a photodiode). The angle at which this occurs together with the depth and half-width of the minimum were determined by the thickness and complex refractive index of the metal film. The magnitude of the evanescent field which arises from the charge density wave decays exponentially in the direction normal to the surface. Consequently, any dielectric layer (such as a peptide overlayer or cell membrane) adhering to the metal film will cause a change in the condition for resonance. By fitting the Fresnel equations, firstly to the date for the uncoated metal film, and then to the metal plus thin film, the thicknesses and complex refractive indices of the metal and peptide overlayer were determined. Typical thickness resolution for the SPR were of the order of 0.01 nm making it an extremely sensitive probe for the surface chemistry of peptides and proteins. By observing changes in reflectivity at a fixed angle of incidence, it is possible to monitor the adsorption of peptides from solution onto a surface and thus obtain time resolved binding of molecules from the bulk to a surface. Another practical advantage of this method is that peptide chemistry can be determined in aqueous environments rather than the ultrahigh vacuums needed for other surface-sensitive techniques (e.g. ESCA).

3. Characterization of Peptide Stability
   a. Fluorescent Tagging of Immobilized Peptides
   5-(and-6)-carboxythtramethylrhodamine succinimidyl ester, i.e. TAMRA SE (Molecular Probes #C-1171), reacts preferentially with amines. TAMRA SE has the advantage of maintaining stability for weeks and is stable in pH's ranging from 4 to 9. The excitation and emission wavelengths of this compound are 546λ and 576λ, respectively. TAMRA SE is made up as a 1 mM solution in DMF. It is then mixed with a pH 8.5 sodium tetraborate buffer in a 1:1 ration for a final solution concentration of 0.5 mM. This is reacted with the samples on a stirrer plate for four hours. Rinsing is done overnight in 4 M urea+0.6% Tween 60.

b. Analysis of Peptide Stability under Physiologic Conditions
   Various immobilized peptides, tagged with fluorescent probes, are exposed to tissue culture media, tissue culture media with 10% serum, and osteoblasts. After 1, 7, 14 and 28 days of culture, substrates are rinsed several times, and assessed for fluorescence using confocal microscopy.

Results

1. Contact Angle

Contact angles on pure gold are greatly effected by hydrocarbons adsorbed from air, but surface energy was performed on these contaminated surfaces anyway as any implants are likely to be maintained in air and are all going to be thus contaminated. Contact angles were measured with ethyleneglycol, glycerol, distilled water and ethanol on a goniometer. Each fluid was placed on the substrate using a syringe with a 26 gauge needle. The smallest drop possible was used to minimize gravitational effects. At least three measurements per liquid-sample combination were taken. The surface energy was calculated using Sacher's method. The results gave us the following surface energies:

| Material | Surface Energy |
| --- | --- |
| Plain Gold: | 27.4 dyne/cm |
| Gold + RGD: | 25.0 dyne/cm |
| Gold + CG: | 81.9 dyne/cm |
| Gold + RGDC: | 42.1 dyne/cm |

On unmodified FEP, water generated a contact angle of approximately 105° indicating an unwettable, low energy surface. RFGD treated FEP showed a contact angle of 60–65° with water confirming the presence of polar hydroxyl groups.

2. Surface Plasmon Resonance

The incubation of a pure gold surface with a 0.22 mM solution of the RGDC peptide results in rapid film formation. Presumably the rapid adsorption is driven by the strong interaction of the cysteine residue of the peptide with the gold surface. The data is shown in FIG. 1.

FIG. 1 is a graph of the observed reflectivity change upon incubation of a clean gold surface. The spectra were fitted using fresnel reflectivity theory. Fitting the bare substrate spectra yielded optical constants for the gold film of: Refractive index $(n,k)=0.26708, -3.304$, Film thickness of 482 Å, Fit error$=8.4\times10^{-3}$. Using these constants for the gold film, the SPR spectra of the RGDC layer was analyzed to obtain the thickness and refractive index of the peptide layer. The refractive index and thickness of the RGDC layer were allowed to vary between sensible limits during the fitting procedure, the best fit to the data yielded the following parameters for the RGDC layer: Refractive index $(n,k)= 1.4665, -0.0992$, Film thickness of 23–25 Å, Fit error$=4.36\times 10^{-3}$.

Figure 2:
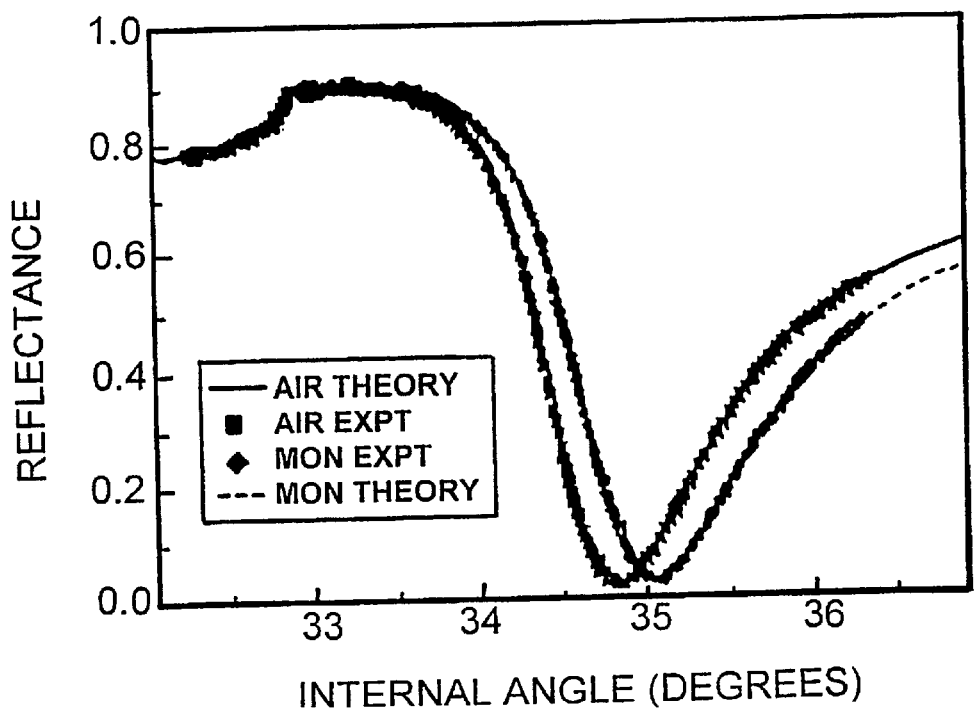
FIG. 2 is a graph depicting the SPR spectra taken in an air ambient before and after adsorption of the RGDC peptide layer.
Figure 3:
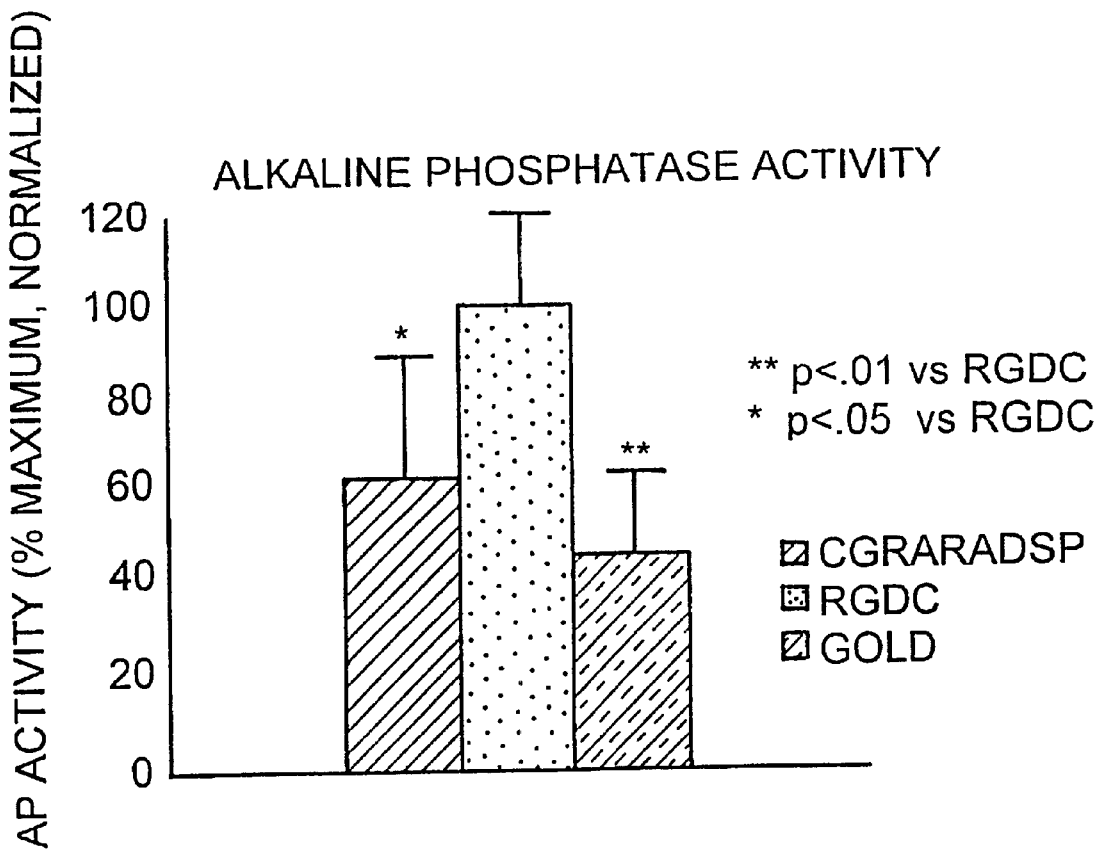
FIG. 3 is a graph depicting alkaline phosphatase activity from osteoblasts cultured on RGDC-gold coated, CGRARADSP-gold coated, and plain gold surfaces.

FIG. 2 depicts a theoretical curve for the RDGC layer which was generated using the above parameters. The film thickness value of 23–25 Å indicates that the peptide molecules are in an upright orientation.

Non-SH containing RGD failed to bind to the gold surface.

Example 2

Evaluation of the Effects of Immobilized Peptides on Osteoblast Differentiation In Vitro Rat calvarial osteoblasts were used as a model system because they have been used extensively in in vitro for studies of bone cell differentiation. These cells undergo a predictable, temporal expression of biochemical and gene markers of the osteoblast phenotype over a three to four week period in culture (Aronow 1990, Harris 1994). Lian et al. have described three phases of osteoblast growth and differentiation in vitro (Breen 1994). The initial phase (days 1–6) involves active cell proliferation and increases in collagen type I gene expression. Matrix maturation occurs over the second week in culture and was accompanied by increased alkaline phosphatase mRNA expression and enzyme activity. The final phase involved cell aggregation into nodules with subsequent mineralization. This period included increased osteocalcin and osteopontin gene expression and protein synthesis. This standard sequence of osteoblast differentiation served as the reference by which experimental substrates were evaluated.

In the proposed study, attachment, morphology, proliferation, biochemical markers (alkaline phosphatase and osteocalcin levels) and gene expression (see below for details) for calvarial osteoblasts were quantified after 7, 14, 21, and 28 days in culture. Biochemical assays and Northern analysis were performed using standard techniques such as those set forth below.

Methods

Rat Osteoblast Isolation

Primary rat calvarial osteoblasts (RCOB) were isolated from post-natal six day old rat pups. The crania were dissected using sterile technique under the tissue culture flow hood. Parietal and frontal bonds were dissected free from the sutures and subjected to collagenase digestion (4×20 min; typeI: type II=6:1) (Boden, 1996). The specific activity of collagenase I and II (Worthington Enzymes, Freehold, N.J.) was 42.5 IU/ml, 88.25 IU/ml in the first digestion and 170 IU/ml, 353 IU/ml for the remaining two digestions (Boden, supra 1996). Cells from the second and third digestions were pooled to form an osteoblast rich suspension. These cells were rinsed, pelleted and plated in MEM (Gibco) with 10% FBS (Hyclone) at a density of 6,510 cells per cm$^2$(Lian, 1990). After confluence, the media was switched from MEM to a mineral rich BGJb media, to which 10% FBS, 50 mg/ml ascorbic acid, and 10 mM Beta Glycerol Phosphate are added (Lian 1990). For sub-cultivated experiments, primary cells were expanded in T-75 flasks with MEM and 10% FBS. After reaching (about 80%) confluence, cells were sub-cultivated with 2.5% trypsin/EDTA and plated at 20,000 per cm$^2$ in MEM+10% FBS (Lian, supra 1990). At day 7, 50 mg/ml ascorbic acid was added to induce collagen I synthesis (Boden, supra 1996). At day 14, the media was switched to BGJb+10% FBS, and 10 mM Beta Glycerol Phosphate.

Peptides

Peptides from Table I were synthesized as described above. Each peptide was coupled to a substrate at a concentration of 0.22M.

Competitive Binding Assays

Experimental and control peptides are added to a suspension of 60,000 RCOB cells in serum free media, at a concentration of 0.05, 0.1 and 0.2 mM. Cells were incubated with soluble peptide for 45 minutes in a humidified 5% $CO_2$, 37° C. environment prior plating onto peptide-immobilized substrates or the appropriate ECM protein. All plated cells were maintained in F12 media with no serum. One or two hours after the time of initial plating, a cell count was completed for each of at least three wells. Cell counting was performed by rinsing several times with DMEM, and using the MTT assay (see below) or by fixing with formalin and performing and performing counts in ten different high powered microscopic fields on each individual substrate.

Cell Counting with MTT Assay

Standard curves were prepared by plating rat calvarial osteoblasts at densities of 100,000, 50,000, 25,000, 10,000 and 5,000 cells/well. Cells were incubated in serum-free Dulbecco's Modified Eagle Media, i.e. DMEM (Gibco) for two hours. Then 3-[4.5-Dimethylthiazol-2-yl]-2,5-diphenyltetrazolium bromide, i.e. MTT (Sigma) in media was added to a final concentration of 0.5 mg.ml. The plates were placed back in the incubator for three hours. Each well was then rinsed with Hanks' Balanced Salt and then 1 ml of 10% Sodium Dodecyl Sulfate, i.e. SDS (Sigma) was added. Cells were covered in aluminum foil to protect it from light and left at room temperature for 12 hours. The SDS solution was then removed, placed into cuvettes, and examined in a Beckman DU-65 spectrophotometer at a wavelength of 570 nm.

For testing peptide-coated substrates, cells were plated at 50,000 cells per well plates. Attachment was evaluated at 20 minutes, 1 hour, 3 hours and 24 hours. At the conclusion of each time oint unattached cells were removed by rinsing three times with HBSS. MTT in serum-free media was added at a concentration of 0.5 mg/ml to perform cell counting and incubator for 3 hours to allow the cells to process the MTT. The plates were then removed and each well given a single HBSS rinse followed by addition of 1 ml of 10% SDS for cell lysis. After 12 hours the SDS solution was removed, placed into cuvettes, and examined in a Beckman DU-65 spectrophotometer at a wavelength of 570 nm.

Cell Morphology With Scanning Electron Microscopy

Substrates with cells were treated with 2% paraformaldehyde+1% gluteralehyde for one hour. Then they were rinsed in 1M PBS and placed in 50%, 70%, 90% and 100% (twice) ethanol for ten minutes each to dehydrate them. The substrates were then immersed in 1:1 ethanol-:hexamethyldisilazane (HMDS) for 30 minutes, and finally were treated with 100% HMDS for thirty minutes and allowed to dry. Samples were fixed onto SEM mounts using a conductive graphite adhesive and sputtered with gold. SEM was performed with a Hitachi S2700 scope.

Cell Proliferation Assay ($^3$H-Thymidine Incorporation)

Primary rat calvarial osteoblasts were plated on substrates in 6-well plates at a density of 20,000 cells/cm$^2$, cultured in MEM media (Gibco)+10%FBS (Hyclone) for 2 days, rinsed with buffered saline, and switched to thymidine-free MEM (Gibco)+0.2% BSA for 1 day (Kim, 1997). On day 4, experimental groups were exposed methyl-$^3$H-thymidine (1 uCi/mmol; DuPont New England Nuclear, Boston, Mass., USA) added 4 hours prior to harvest at 96 hours. Cells were harvested and specific radioactivity (cpm) measured using a scintillation counter. Briefly, cells were washed 3 times with ice-cold PBS to remove excess label, trypsinized, spun down into a pellet, and lysed with 120 ul phosphate buffered 1% nonidet P-40 (Sigma). One hundred microliters of each sample were mixed with 800 ul 0.2% BSA, 100 ul 75% trichloroacetic acid (TCA), and centrifuged. Supernatant was removed and the pellet was centrifuged again with 1 ml 7.5% TCA. The pellet was then solubilized in 900 ml 0.1 N NaOH at 37° C. overnight and neutralized with 100 ul 1N Hcl. Counts were normalized with DNA and expressed as cpm/ug DNA. All data was normalized using total DNA. A fluorometric DNA assay (Arronow, 1990) was performed on the remaining 20 ul aliquots of cell lysate using a TKO 100 mini-fluorometer (Hoefer, San Francisco, Calif., USA) to normalize cell counts. Samples were incubated with benzimidazole (Hoechst 33258; Pharmacia Biotech, Piscataway, N.J.) and fluorescence quantified. DNA content was obtained using a calf thymus DNA (Pharmacia Biotech) standard curve.

Alkaline Phosphatase Activity

Alkaline phosphatase (AP) activity of cell lysates was determined by an established enzymatic conversion assay using p-nitrophenol phosphate as a substrate (Spiess). The enzyme activity was expressed as nanomoles of p-nitrophenol produced per minute per milligram of protein (nmol/min/mg protein). The protein content was determined using the Biorad protein assay kit (Biorad, Hercules, Calif.) using BSA as the standard.

Alkaline Phosphatase Staining

Osteoblasts were fixed in buffered 2% paraformaldehyde for 24 hours. Before staining, cells were rinsed in distilled water. Alkaline phosphatase staining was visualized by incubating the cells for 30 min in 0.1 M Tris HCL pH 8.5 containing 0.4 mg/ml naphthol AS-MX phosphate+1 mg/ml Fast Blue BB salt. Cells were then rinsed in 1 M PBS and preserved in PBS glycerol. The intensity of osteoblasts stained with alkaline phosphatase was qualitatively assessed by counting the number of osteoblasts per 10× field.

Osteocalcin RIA

Osteocalcin levels were assessed after removing aliquots of conditioned media from cell cultures of experimental groups using a radioimmunoassay (RIA) for rat osteocalcin (rat osteocalcin kit, BTI, Stoughton, Mass.) according to a previously described method (Gundberg 1984). Purified rat osteocalcin, goat anti-rat osteocalcin antibody, normal goat nonimmune serum, donkey anti-goat 2nd antibody, RIA buffer and [I-125] rat osteocalcin were used as reagents for RIA as provided by BTI. The standards and the samples were incubated overnight with a known quantity of goat anti-rat osteocalcin antibody followed by another incubation with [I-125] rat osteocalcin (approx. 20,000 cpm). The tubes were incubated (2 hours) with donkey anti-goat 2nd antibody, centrifuged, and pellets counted (cpm) using a gamma counter. A standard curve was generated and sample concentration of osteocalcin (ng/tube) obtained.

Extracellular Matrix Protein and Integrin Gene Expression by Northern Analysis

During the course of bone development and metabolism, a variety of osteoblast growth and differentiation factors are known to be expressed in vitro (Ibaraki, 1992) and in vivo (Jingushi, 1991, Sandberg, 1993). Integrin gene expression is also modulated.

1. RNA extraction

RNAzolTM (Tel-Test, Friendswood, Tex.) reagent was added to the cell cultures removed of media and then shaken gently until a viscous, opaque liquid was seen. The contents were transferred to ice cold tubes to which chloroform was added and vortexed. After centrifugation for 10 min. at 10,000 rpm, the top aqueous phase was re-extracted with fresh RNAzol and chloroform. After a series of re-extraction and centrifugations, the cell pellet was washed in 70% ethanol and resuspended in 50 ul TE buffer. The concentrations and purity of the RNA is measured with a spectrophotometer using the ratio of $A^{260}$ and $A^{280}$.

2. RNA gel

RNA (15–20 ug) from specific experimental groups was separated on the basis of size with a denaturing 1.2% agarose (Formaldehyde) gel electrophoresis. All RNA gels were run for 3 hours at 100 V and photographed using an ultraviolet light source. A TurboBlot % kit was used to transfer the RNA from the gel to the nylon (blotting) membrane. The RNA was then cross linked and baked on permanently onto the membrane (under a UV lamp and baked at 120° C. for 15 minutes).

3. Hybridization & Detection cDNA probes for rat alkaline phosphatase and rat osteocalcin were kindly provided by Dr. J. Lian (University of Massachusetts, Worcester, Mass.). The cDNA probes for α5 and β1 integrins were provided by Dr. E. Ruoslahti (Cancer Institute, La Jolla, Calif.). The cDNA probe for bone sialoprotein was provided by Dr. J. Sodek (University of Toronto, Toronto, Canada), while the cDNA probe for collagen was provided by Dr. B. Kream (University of Connecticut, New London, Conn.). The cDNA probes for GAPHDH, beta-actin, human osteopontin, and human osteonectin were obtained from the American Type Culture Collection (ATCC).

The membranes were treated with various buffers (5×SSPE, 50% formamide, 2% SDS and 10×Dengardt's solution). The hybridized probes were radioimmunodetected through the use of $^{32}P$. The membranes were then reacted with the cDNA probes and hybridized with the probes at 68° C. overnight and washed through a series of (2×SCC & 0.1% SDS) solutions. After the washing steps, the membrane were exposed with x-ray film. The mount of RNA was quantified through comparison with the known amount of RNA transcript that was loaded in the lane on the gel. The size of the RNA molecule was calculated by measuring the distance migrated and comparing it to the standard. All mRNA hybridization experiments were performed twice with each cDNA probe. All cDNA was normalized to GAPDH.

Results

Cell Attachment

RCOBs in DMEM with 10% fetal bovine serum were plated at 25,000 per square centimeter. Visual analysis revealed higher levels of attachment at 20 minutes on the RGDC treated substrates. This was quantitatively confirmed using an MTT assay which showed that at 20 minutes there was 100% greater attachment to the RGDC surface compared with gold and RGD treated surfaces. Similar to the gold surface RCOBs showed much greater attachment when cultured on RGDC-FEP modified surfaces than on unmodified FEP.

Alkaline phosphatase Activity

Alkaline phosphatase activity revealed that RGDC coupled surfaces produced the highest levels of this enzyme. CGRARADSP (control peptide) and plain gold substrates produced values which were not significantly different from one another. The results are shown in FIG.

Osteocalcin mRNA Assay

At nine days Osteocalcin mRNA was heavily expressed on RGDC-gold coated surfaces but was not observed on Gold and CG-gold coated surfaces. After fourteen days RGDC still showed higher levels than the others, and at nineteen days all substrates were virtually identical. Additionally it was found that Osteocalcin mRNA expression was induced earlier in cells which were grown on the prosthetic implants of the invention having a peptide coated gold surface than on the polymeric prosthetic implants (FEP) coated with the identical peptide. Osteocalcin is not expressed at 9 days when cells are grown on the peptide coated polymer surface. This finding suggest that the gold surface is also important to the regulation of bone morphogenesis.

Osteocalcin Protein Synthesis

It is also important to determine how immobilized proteins influence protein synthesis. Osteocalcin was evaluated since it is a marker of bone cell differentiation and because radioimmunoassays (RIA) are commercially available (Arono, 1990; Gundberg, 1984; Ibaraki. 1992).

After 14 days in culture, RGD-FEP coupled membranes induced significantly higher levels of osteocalcin synthesis compared with all other groups. The unique ability of RGD-FEP coated substrates to enhance osteocalcin synthesis is consistent with increased RCOB mRNA expression seen at day 14. The RGE is closest to RGD in stimulating osteocalcin synthesis. RAD peptide was similar to OH and TCP.

ECM and Integrin Gene Expression for Sub-Cultivated RCOBs

Evaluation of matrix protein gene expression provides a quantitative method of assessing cell differentiation in a temporal fashion. The normal pattern of RCOB gene expression has been reported for primary and subcultured cells (Aronow, 1990; Breen, 1994; Lynch, 1995 and others). It has been demonstrated that subcultured RCOB display a "right-shifted" pattern of gene expression compared to primary cells.

Alkaline Phosphatase

On day 9 Alkaline Phosphatase gene expression was observed on all substrates at minimal levels but was significantly higher on RGDC coated gold surfaces. No change over the time period studied in Alkaline Phosphatase levels was observed in the cells cultured on FEP surfaces.

Bone Sialoprotein

Similar to Alkaline Phosphatase gene expression, bone sialoprotein gene expression was much higher on RGDC coated gold surfaces than on gold surfaces alone or gold surfaces coated with a control peptide. Bone sialoprotein gene expression was not observed in cells cultured on FEP surfaces.

$\beta_1$ integrin $\beta_1$ integrin gene expression was observed on all substrates at minimal levels but was significantly higher on RGDC coated gold surfaces. By the 14th day of culture, the mRNA signal detected from cells cultured on RGDC coated gold surfaces had shifted from one band to two bands. This shift to two bands was not detected in RNA isolated from cells cultured on any of the other surfaces.

$\alpha_5$ integrin $\alpha_5$ integrin gene expression was observed in cells cultured on RGDC coated gold surfaces but was not detected in cells cultured on any other surfaces. Similar to $\beta_1$ integrin, the expression pattern of $\alpha_5$ integrin was observed to shift on day 14 from a single band to a double band.

Example 3

Peptide Modified Surfaces Support Focal Adhesion Formation

The cytoplasmic domains of integrins are relatively short (approximately 50 amino acids), but are sufficiently long enough to interact with cytoskeletal proteins in focal contacts (or focal adhesions or adhesion plaques). Focal adhesions are connected to the nucleus via microspikes or bundles of actin filaments. Several experiments provide strong evidence for these connections between the exterior and interior of the cell. In fluorescence photobleaching, integrins were fluorescently labeled, then overexposed to form a bleached spot. This bleached area did not move, showing the restricted mobility of integrins in focal contacts (Duband, 1986). Solowska (1989) showed that expression of a mutant form of avian integrin beta 1 subunit lacking the cytoplasmic domain produces hybrid heterodimers which, while efficiently exported to the cell surface and still capable of binding fibronectin, do not localize efficiently in focal adhesions. This further implicates the cytoplasmic domain of the beta 1 subunit in interactions required for cytoskeletal organization.

The cytoskeletal proteins present in focal adhesions are well-defined: vinculin, talin, and alpha actinin serve as links between integrins and the bundles of actin filaments (stress fibers) of the cytoskeleton. Evidence in the literature suggests that focal adhesions are required for signal transduction from the ECM to the nucleus of the cell. Upon integrin-mediated adhesion to ECM proteins, focal adhesion kinase (FAK), a tyrosine kinase, becomes phosphorylated (Schneider, 1994). Activation of FAK is believed to initiate a signaling pathway to the nucleus, resulting in changes in gene expression.

Both fibronectin and type I collagen are present in the extracellular matrix. We tested our monolayer surface of active peptides to determine wather it can stimulate focal adhesion formation in the absence of serum in a similar manner to the interaction between the cell and the related parent protein of the peptide sequence. In order to evaluate the influence of active portions of these parent proteins on osteoblast cell response in short time frames we modified gold coated coverslips with the fibronectin related peptide: RGDC or the collagen related peptide: DGEAGC, and evaluated the ability of these surfaces to support focal adhesion formation at two time points, 3 and 24 hours, under serum free conditions.

Methods

Fibronectin/RGDC Study

Experimental groups included RGDC, RADC, fibronectin adsorbed to gold, plain gold, and plain glass surfaces. Gold substrates were manufactured by evaporating 80 angstroms of titanium to 12 mm glass coverslips (Fisher), followed by a 500 angstrom layer of gold. To couple cysteine terminated peptides to the gold substrates, a 0.22 mM solution of the desired peptide was solubilized in a 1:1 mixture of distilled water and ethanol. These substrates were then incubated overnight. Plain gold controls were exposed to ethanol and distilled water as well. Fibronectin substrates were produced by incubating gold coverslips with 10 µg/ml of fibronectin (Collaborative Biomedical Products, Bedford, Mass.) for 60 minutes, followed by 10 mg/ml bovine serum albumin (BSA) (Sigma, St. Louis, Mo.) for 30 minutes to cover any non-specific binding sites. All coverslips were then washed three times in HBSS to remove any non-adsorbed protein (Puleo, 1991). Primary rat calvarial osteoblasts were isolated according to protocol and seeded for periods of 3 or 24 hours in serum free or serum conditions. At each time point cells were rinsed in warm PBS, fixed in 3.7% paraformaldehyde for 30 minutes, and rinsed several times with HBSS. Vinculin and actin were labeled via the following protocol: nonspecific sites were blocked in 5% BSA for 30 minutes, cells were then permeabilized with 0.2% Triton X-100 (Fisher) for 10 minutes, incubated in a 1:50 mouse anti-human vinculin antibody solution (Sigma St. Louis, Mo.), blocked for 30 minutes, and incubated with a anti-mouse rhodamine secondary antibody (1:50) and FITC conjugated phalloidin (Molecular Probes).

Type I Collagen/DGEAGC

Experimental groups included DGEAGC and rat tail type I collagen adsorbed to gold, plain gold, and plain glass surfaces. Gold substrates were manufactured by evaporating 80 angstroms of titanium to 12 mm glass coverslips (Fisher), followed by a 500 angstrom layer of gold. To couple cysteine terminated peptides to the gold substrates, a 0.22 mM solution of the desired peptide was solubilized in a 1:1 mixture of distilled water and ethanol. These substrates were then incubated overnight. Plain gold controls were exposed to ethanol and distilled water as well. Type I collagen substrates were produced by incubating gold coverslips with 10 µg/ml of collagen (Collaborative Biomedical Products, Bedford, Mass.) for 60 minutes, followed by 10 mg/ml bovine serum albumin (BSA) (Sigma, St. Louis, Mo.) for 30 minutes to cover any non-specific binding sites. All coverslips were then washed three times in HBSS to remove any non-adsorbed protein (Puleo, 1991). Primary rat calvarial osteoblasts were isolated according to protocol and seeded for periods of 3 or 24 hours in serum free or serum conditions. At each time point cells were rinsed in warm PBS, fixed in 3.7% paraformaldehyde for 30 minutes, and rinsed several times with HBSS. Vinculin and actin were labeled via the following protocol: nonspecific sites were blocked in 5% BSA for 30 minutes, cells were then permeabilized with 0.2% Triton X-100 (Fisher) for 10 minutes, incubated in a 1:50 mouse anti-human vinculin antibody solution (Sigma St. Louis, Mo.), blocked for 30 minutes, and incubated with an anti-mouse rhodamine secondary antibody (1:50) and FITC conjugated phalloidin (Molecular Probes).

Results

At three hours, vinculin staining revealed the ability of RGDC peptide modified surfaces to support focal adhesion formation in the absence of serum. Fibronectin coated surfaces also supported focal adhesion formation. Cells on both surfaces tended to have vinculin staining located at the cell periphery in the form of distinct plaques at the cell tips. No vinculin staining was observed on cells plated on RADC, glass or plain gold.

At three hours, vinculin staining revealed the ability of DGEAGC peptide modified surfaces to support focal adhesion formation in the absence of serum. Collagen coated surfaces also supported focal adhesion formation. Cells on both surfaces tended to have the brightest vinculin staining located at the cell periphery in the form of either distinct plaques or groups of strands at the cell tips. No vinculin staining was observed on cells plated on glass or plain gold.

Example 4

Evaluation of the Effect of Immobilized Peptides on Osteoblast Differentiation

We have shown above that in vitro, peptide modified surfaces can influence short and long term cell responses like attachment, shape and function. We also conducted a study to evaluate the amount of bone formed in response to gold coated titanium rods modified with the peptide sequence Arg-Gly-Asp-Cys (RGDC). Titanium rods coated with gold, FEP rods and uncoated titanium rods were implanted bilaterally into the distal medial femoral condyle of adult rats and evaluated at 2, 4, 8, and 24 weeks post-implantation. The experiments are discussed below.

In vivo
Modification and Characterization of Peptide-grafted FEP Rods and Titanium Titanium rods were generously donated by Osteonics Corporation (NJ, USA). Rods were cleaned according to ASTM standards before coating them with a 500 layer of gold using an electron beam evaporator. Rods were immersed in a 0.22 M solution (1:1 ethanol:water) of RGDC (American Peptide Company, Sunnyvale, Calif.) overnight at room temperature and stored in sterile PBS, using the techniques described above, until the time of surgery. FEP rods were coupled with peptides using the techniques described above. Un-coated titanium rods are used as a control. Briefly, the materials were initially cleaned in a radio frequency glow discharge chamber using a flow-through system with an Argon atmosphere. The alloys were immediately transferred to a nitric acid bath for 30 min in order to passivate the surface according to ASTM standards (Puelo 1994). The samples were transferred to a gold evaporation chamber and reacted with peptides as described above. Characterization of gold coated titanium materials, FEP and titanium materials were performed as described above.

Peptide-coated Materials and uncoated Titanium Implanted in Rat Femur Sites

Quantitative histomorphometric analysis and pull-out biomechanical testing was conducted at 2 and 4 weeks on implants inserted bilaterally into the femoral canal of 20 adult Sprague Dawley rats. Parameters evaluated included the area and thickness of new bone formed around the implants, the percent of the implant covered by new bone, and the interfacial shear strength at the bone/implant interface. The distal rat femur provides a well-studied site for bone material interactions and offers a sufficient bony area to implant small specimens. Adult Sprague Dawley rats weighed an average of 415±12 g at the time of surgery. The rats were anesthetized using a 0.5 ml intraperitoneal injection of Nembutal and 0.1 ml of Cefazolin was injected intramuscularly at the surgical site. Reaming of the distal end of the femoral canal was done first by inserting an 18 gauge needle down the femoral shaft, followed by irrigation of the femur with sterile saline, reaming with a 1.5 mm drill bit using a hand held drill to prevent thermal necrosis, irrigation, reaming with a 16 gauge needle, irrigation, and final reaming of the outer cortex with a 14 gauge needle. The rod was then press fit into place with the outermost end below the condylar surface, in each case. RGDC coated rods were placed at random with one control rod and one experimental rod being placed bilaterally in each animal. Lateral and anterior-posterior X-rays were taken postoperatively to assess rod position. The fascia and skin are closed in standard fashion using 5-1 vicryl bioresorbable sutures.

Histological evaluation

After mechanical testing, femurs were removed from the dental plaster and stored in phosphorous buffered saline for 24 hours until fixation in 3.7% paraformaldehyde for 48 hours at room temperature. Decalcification was performed according to a method described by Frank, et al, (1993). Briefly, bones were allowed to demineralize over the course of 2 weeks in 15% formic acid solution at 4 ûC. Bones were rinsed and permbealized in 6.8% sucrose/PBS solution overnight. Dehydration of bones was conducted as follows: 20 minutes per ethanol concentration: 70, 80, 90, 95%. Bones were sectioned from the growth plate at 2, 5, 8, 12, and 15 mm and embedded in Historesin (Leica, Germany) for histological analysis. Briefly, bones were infiltrated for 48 hours at 4 ûC and then embedded overnight. 5 $\mu$m sections were made. Specimens were stained using Hematoxylin and Eosin and GomoriÕs trichrome stains. Quantitative histomorphometrical analysis was conducted on bone cross sections sectioned at 5 mm using IP Lab Software. Images of bone cross sections were captured by microscope and imported into a computer via a CCD camera. Parameters measured by two independent observers included the perimeter of new bone formed, the area of new bone, the perimeter availabe for new bone formation and the diameter of the hole where the implant was. Some sections were not analyzed due to histological sectioning tears. Also, if the amount of new bone formed around the implant was not clear (e.g. implant abutting cortex) that portion of the cross section was not included for analysis.

Biomechanical Pull-out Testing

The biomechanical pull-out strength between the bone/RGDC and bone/Au was measured using the widely imployed pull-out test (Chae et al in 1992 and Tisdel et al in 1994, Branemark & Berzin). All testing was performed in a blinded fashion.

Animals were sacrificed at 2 and 4 weeks postoperatively. Animals were first anesthetized with a 0.5 ml intraperitoneal injection of Nembutal and then sacrificed by a 0.5 ml intracardial injection of Nembutal. Mechanical testing of all femurs was conducted the same day as sacrifice. Immediately after explantation, femurs were cleaned of all soft tissue, x-rayed and prepared for mechanical testing or histological evaluation. A total of 23 animals were evaluated. Three animals were excluded, one because of death during surgery, and two because of pathologic fractures. For mechanical testing at 2 weeks, 7 animals were assessed while 8 animals were assessed at 4 weeks. Histological evaluations were carried out on 8 femurs used for mechanical testing at each time point. An alignment jig was designed in order to insure a pure tensile force was applied to the rod. Dental plaster was used to hold the proximal portion of the femur in place during testing. Modified needle-drivers gripped the end of the implant as it was pulled from the bone at a crosshead speed of 5 m/min. The force required to break the interface was recorded and the portion of the implant estimated to be contact bone was also recorded.

Results

The in vivo studies involving implantation of FEP coated and uncoated materials indicate that implants coated with a bioactive molecule such as RGDC have accelerated or enhanced bone ingrowth. Briefly, the peptide coated implants demonstrated a significantly greater percentage of their surface perimeter covered with bone. Additionally the biomechanical pull-out strength was significantly greater for the peptide coated implants versus the uncoated implants.

By 4 weeks the average pull-out force of peptide modified rods was 38% greater than gold control rods although this difference was not statistically significant (Table 1). Furthermore, at 4 weeks there was significantly ($P<0.01$) more new bone area formed around RGDC implants and the thickness of this new bone formed around RGDC implants differed significantly ($P<0.01$) from Au controls at both 2 weeks (26.2 microns±1.9 vs. 20.5 microns±2.9) and 4 weeks (32.7 microns±4.6 vs. 22.6 microns±4.0)

Biomechanical

No statistical differences were found between peptide modified and gold control rods for the interfacial shear strength at 2 and 4 weeks respectively. It should be noted however, that the mean of the peptide modified group at 4 weeks was 38% higher than the control group (Table 1).

TABLE 1

| | Interfacial Shear Strength (MPa) | |
|---|---|---|
| | 2 weeks Postimplantation | 4 weeks Postimplantation |
| Gold coated rods | 0.17 ± 0.09 | 0.13 ± 0.06 |
| RGDC modified rods | 0.16 ± 0.06 | 0.18 ± 0.07 |

Histology

Although there were not a significant differences in the pull-out forces between groups, there were significant differences in the amount of bone (thickness and area) formed around the implants at two and four weeks. There were no differences in the percent of the implant cross section covered by bone (76±14%, 74±5%) for the RGDC and Au groups respectively. At four weeks more of the implant was covered by bone but the percent of the implant cross section covered by bone for the RGDC and Au groups did not differ significantly (92±4% vs. 90±7%). The area of new bone formed around RGDC implants was not significantly more compared to Au controls at 2 weeks (0.108 $\mu m^2$±0.026 vs. 0.082 $\mu m^2$±0.017), but by 4 weeks there was a significantly ($P<0.01$) more area of new bone formed around RGDC implants (0.16 $\mu m^2$±0.016 vs. 0.108 $\mu m^2$±0.023). The thickness of new bone formed around RGDC implants differed significantly ($P<0.01$) from Au controls at both 2 weeks (26.2 $\mu m$±1.9 vs. 20.5 $\mu m$±2.9) and 4 weeks (32.7 $\mu m$±4.6 vs. 22.6 $\mu m$±4.0).

Example 5

Peptides Act Synergistically to Increase Bone Cell Responsiveness

The response of bone cells to peptide combinations showing synergy or high individual levels of activity is evaluated in vitro and in vivo using methods described above with combinations of peptides rather than a single peptide. Two non-adjacent peptide sequences from fibronectin, including RGD and PHSRN, a so-called synergy sequence, exhibit synergistic behavior (Aota 1994; Akiyama, 1995). These experiments can be used to identify, track and quantify different peptides on the same membrane.

REFERENCES

1. Aota, S., et al. (1994), "The short amino acid sequence Pro-His-Ser-Arg-Asn in human fibronectin enhances cell-adhesive function," *J. Biol. Chem.* 269(40):24756–61.
2. Akiyama, S. K., et al. (1995), "Function and Receptor Specificity of a Minimal 20 Kiladalton Cell Adhesive Fragment of Fibronectin," *Cell Adhesion and Communication* 3:13–25.
3. Akiyama, S. K., et al. (1995), "Fibronectin and integrins in invasion and metastasis," *Cancer Metastasis Rev.* 14(3):173–189.
4. Aronow, M. A., et al. (1990), "Factors that Promote Aggressive Development of the Osteoblast Phenotype in Cultured Fetal Rat Calvaria Cells," *Journal of Cellular Physiology* 143:213–221.
5. Bartfeld, N. S., et al. (1993), "The v3 Integrin Associates with a 190-kDa Protein That is Phosphorylated on Tyrosine in Response to Platelet-Derived Growth Factor," *Journal of Biological Chemistry* 268(23): 17270–17276.
6. Bassuk, J. A., et al. (1993), "Molecular analysis of chicken embryo SPARC (osteonectin)," *Eur. J. Biochem* 218(1):117–127.
7. Bautista, D. S., et al. (1994), "Inhibition of Arg-Gly-Asp (RGD)-mediated Cell Adhesion to Osteopontin by a Monoclonal Antibody against Osteopontin," *Journal of Biological Chemistry* 269(37):23280–23285.
8. Beer, J. H., et al. (1992), "Immobilized Arg-Gly-Asp (RGD) peptides of varying lengths as structural probes of the platelet glycoprotein Iib/IIIa receptor," *Blood* 79:117–128.
9. Bengston, A., et al. "Anaphylatoxin release in association with methylmethacryl fixation of hip prostheses," *JBJS* 69; 46 (1987).
10. Boden, S. D. (1996), "Differential Effects and Glucocorticoid Potentiation of Bone Morphogenetic Protein Action During Rat Osteoblast Differentiation in vitro," *Endocrinology* 137(8):3401–3407.
11. Boudreau, N., et al. (1994), "From laminin to lamin: regulation of tissue-specific gene expression by the ECM," *Forum*.
12. Breen, E. C., et al. (1994), "TGFB Alters Growth and Differentiation Related Gene Expression in Proliferating Osteoblasts in vitro, Preventing Development of the Mature Bone Phenotype," *J. of Cellular Physiology* 160:323–335.
13. Briggs, D., "Handbook of x-ray and photoelectron spectroscopy," London: Heyden and Sons(1977).
14. Brighton, C. T., et al. (1992), "Identification of Integrin Cell-Substratum Adhesion Receptors on Cultured Rat Bone Cells," *J. Orthopaedic Research* 10:766–773.
15. Callen, B. W., et al. (1993), "Behavior of primary bone cells on characterized polystyrene surfaces," *Journal of Biomedical Materials Research* 27:851–859.
16. Cameron, H. U. (1986), "Six year results with a microporous-coated metal hip prosthesis," *Clin. Ortho.* 208:81–83.
17. Cardarelli, P. M., et al. (1992), "The Collagen Receptor 21, from MG-63 and HT1080 Cells, Interacts with a Cyclic RGD Peptide," *Journal of Biological Chemistry* 267(32):23159–23164.
18. Cheng, S. L., et al. (1995), "Expression and Regulation of Integrins During the Differentiation of Normal Human Osteoblasts and Human Bone Marrow Stromal Cells," *17th Annual Meeting of the American Society for Bone and Mineral Research* (T223).
19. Chen, S., et al. (1994), "Design and Synthesis of Novel Cyclic RGD Containing Peptides as Highly Potent and Selective Integrin aiibB3 Antagonists," *J. of Medicinal Chemistry* 37(1).
20. Cheresh, D. A. (cd.), et al. (1994), *Integrins: Molecular and Biological Responses to the Extracellular Matrix,* Academic Press, Inc., San Diego, Calif.
21. Chorev, M., et al. (1995), "Approach to discovering novel therapeutic agents for osteoporosis based on integrin receptor blockade," *Biopolymers* 37(6):367–375.
22. Clover, J., et al. (1992), "Integrin subunit expression by human osteoblasts and osteoclasts in situ and in culture," *J. Cell Sci.* 103:267–271.
23. Collins, D. N., et al., "Porous-coated anatomic total knee arthroplasty: a prospect analysis comparing cemented and cementless fixation," *Clin. Orth.*, 267; 128 (1991).
24. Collier, J. P., et al. "Macroscopic and microscopic evidence of prosthetic fixation with porous-coated materials," In Instructional Course Lecture, The American Academy of Orthopaedic Surgeons, 40; 97–99 (1991).
25. Craig, W. S., et al. (1995), "Concept and Progress in the Development of RGD-Containing Peptide Pharmaceuticals," *Biopolymers* 37:157–175.
26. Danilov, Y. N., et al. (1989), "Arg-Gly-Asp)n-Albumin Conjugates as a Model Substratum for Integrin-Mediated Cell Adhesion," *Experimental Cell Research* 182:186–196.

27. Davies, J. E. (ed.) (1991), *The Bone-Biomaterial Interface*, University of Toronto Press, Toronto, Ont.
28. Dedhar, S. (1989a), "Regulation of expression of the cell adhesion receptors, integrins, by recombinant human interleukin-1 in human osteosarcoma cells. Inhibition of cell proliferation and stimulation of alkaline phosphatase activity," *J. Cell. Physiol.* 138:291–299.
29. Dedhar, S. (1989b), "Signal transduction via the beta-1 integrins is a required intermediate in interleukin-1 induction of alkaline phosphatase activity in human osteosarcoma cells," *Exp. Cell Res.* 183:207–214.
30. Dee, K. C., et al. (1996), "Conditions which promote mineralization at the bone-implant interface: a model in vitro study," *Biomaterials* 17:209–215.
31. Dieckgraefe, B. K. (1996), "Immunolocalization of alpha-integrin subunits and extra cellular matrix components during human colonic organogenesis," *Gastroenterology* 110(1):58–71.
32. Dresner-Pollak, et al. (1994), "Blockade of Osteoclast-Mediated Bone Resorption Through Occupancy of the Integrin Receptor: A Potential Approach to the Therapy of Osteoporosis," *Journal of Cellular Biochemistry* 56:323–330.
33. Ducheyne, P., et al. "Influence of a functional dynamic loading on bone ingrowth into surface pores of orthopedic implants," *J. Biomed. Mater. Res.* 11; 811–818, 1974.
34. Duschl, C., et al. (1994), "Biological Addressable Monolayer Systems Formed by Templates of Sulfur-Bearing Molecules," *Biophysical Journal* 67:1229–1237.
35. Ekblom, P., et al. (1991), "Laminin isoforms and their receptors in the developing kidney," *Am-J-Kidney-Dis.* 17(6):603–5.
36. Frenette, P. S., et al. (1996), "Molecular Medicine: Adhesion Molecules—Part I," *New England Journal of Medicine* 334(23):1526–1529.
37. Freshney, R. I. (1987), *Culture of Animal Cells: A Manual of Basic Technique*, Wiley-Liss, New York, N.Y.
38. Friedman, R. J., et al. (1993), "Current concepts in orthopaedic biomaterials and implant fixation," *J. Bone Joint Surg.* 75A:1086–1109.
39. Frost, R. G. (1981), "Covalent immobilization of proteins to N-hydroxysuccinimide ester derivatives of agarose. Effect of protein charge on immobilization," *Biochem-Biophys-Acta* 670(2):163–169.
40. Galante, J. O., et al. "The biologic effects of implant materials," *J. Orth. Res.* 9; 760, 1991.
41. Gehsen, K., et al. (1988), "Inhibition of in vitro tumor cell invasions by Arg-Gly-Asp-containing synthetic peptides," *J. Cell. Biol.* 106:925–930.
42. Genovese, C., et al. (1994), "Construction of DNA sequences complementary to rat $\alpha_1$ and $\alpha_2$ collagen mRNA and their use in studying the regulation of type I collagen synthesis by 1,25-di-hydroxyvitamin D.", *Biochemistry* 23:6216–6221.
43. Giancotti, F. G., et al. (1990), "Elevated levels of the $\alpha_5\beta_1$ fibronectin receptor suppress the transformed phenotype of chinese hamster ovary cells," *Cell* 60:849–859.
44. Ginsberg, M., et al. (1988), "Cytokines, integrins, and platelets," *Thromb. Haemost.* 59:1–6.
45. Ginsberg, M., et al. (1985), "Inhibition of fibronectin binding to platelets by proteolytic fragments and synthetic peptides which support fibroblast adhesion," *Journal of Biological Chemistry* 260(7):3931–3936.
46. Glass, J. R., et al. (1996), "Characterization of a hyaluronic acid-Arg-Gly-Asp peptide cell attachment matrix," *Biomaterials* 17:1101–1108.
47. Gohel, A., et al. (1993), "Involvement of integrins in osteocyte formation: Modulation by glucocorticoids and insulin-like growth factor I," *Molec. Biol. Cell* 4:292a.
48. Good, R. J., "Contact angles and surface free energy of solid," New York: Plenum Press, 1979.
49. Graf, J., et al. (1987), "Identification of an Amino Acid Sequence in Laminin Mediating Cell Attachment, Chemotaxis, and Receptor Binding," *Cell* 48:989–996.
50. Gronowicz, G., (1995a), "Integrin Regulation of c-fos Expression in Osteoblasts," *17th Annual Meeting of the American Society for Bone and Mineral Research* (T234).
51. Gronowicz, G., et al. (1995b), "Glucocorticoids Inhibit the Attachment of Osteoblasts to Bone Extracellular Matrix Proteins and Decrease B1 Integrin Levels," *Endocrinology* 136(2):598–608.
52. Gronowicz, G. A., et al. (1994), "Synthetic peptide containing Arg-Gly-Asp inhibits bone formation and resorption in a mineralizing organ culture system feral rat parietal bones," *J. Bone Mineral Res.* 9(2):193–201.
53. Grzesik, W., et al. (1994), "Bone matrix RGD glycoproteins: immunolocalization and interaction with human primary osteoblastic bone cells in vitro," *J. Bone Mineral Research* 9(4):487–496.
54. Grzesik, W., et al. (1995), "Interaction of Human Bone Cells with Synthetic Peptides Derived from Bone Salioprotein Differing in their Spatial Conformation," *17th Annual Meeting of the American Society for Bone and Mineral Research* (M268).
55. Gundberg, C. M., et al. (1984), "Osteocalcin isolation, characterization and detection," *Methods Enzymol.* 107:517–544.
56. Haddad, R. J., et al. "Current concepts review: Biological fixation of porous-coated implants," *J. Bone and Joint Surg.,* 69-A; 1459–1466, December 1987.
57. Han, I. I., et al. (1994), "A Study of the reproducibility of the MTT test," *Journal of Materials Science: Materials in Medicine* 5:154–159.
58. Hart, I., et al. (1995), *Cell Adhesion and Cancer,* Cold Spring Harbor Laboratory Press: Plainview.
59. Healy, K. E., et al. (1996), "Kinetics of bone cell organization and mineralization on materials with patterned surface chemistry," *Biomaterials* 17(2): 195–208.
60. Hearn, M. T. W. (1987), "1,1-Carbonyldiimidazole-Mediated Immobilization of Enzymes and Affinity Ligands," *Methods in Enzymology* 135:102–117.
61. Hirano, Y., et al. (1991), "Synthesis and cell attachment activity of bioactive oligopeptides: RGD, RGDS, RGDV, RGDT," *J. Biomedical Materials Research* 25:1523–1534.
62. Hoffman, A. S. (1992), "Molecular engineering of biomaterials in the 1990's and beyond: a growing liaison of polymers with molecular biology," *Artificial Organs* 16(1):43–49.
63. Horowitz, S. M., et al., "Study of the mechanism by which mechanic failure of methylmethacrylate leads to bone resorption," *JBJS* 75A; 802, June 1993.
64. Howlett, R., et al. (1994), "Mechanism of initial attachment of cells derived from human bone to commonly used prosthetic materials during cell culture," *Biomaterials* 15(3):213–222.
65. Hughes, D. E., et al. (1993), "Integrin expression in human bone," *J. Bone Mineral Research* 8(5):527–533.
66. Humphries, M. J., et al. (1986), "A synthetic peptide from fibronectin inhibits experimental metastasis of murine melanoma cells," *Science* 233:467–470.
67. Hynes, R. O. (1992), "Integrins: Versatility, Modulation, and Signalling in Cell Adhesion," *Cell* 69:11–25.
68. Hynes, R. O. (1987), "Integrins: a family of cell surface receptors," *Cell* 48:549–54.
69. Ibaraki, K., et al. (1992), "Bone matrix mRNA expression in differentiating fetal bovine osteoblasts," *Journal of Bone and Mineral Research* 7(7):743–754.

70. Ito, Y., et al. (1991), "Materials for enhancing cell adhesion by immobilization of cell-adhesive peptide," *Journal of Biomedical Materials Research* 25:1325–1337.
71. Iwamoto, Y., et al. (1988), "YIGSR, a synthetic laminin pentapeptide, inhibits experimental metastasis formation," *Science* 238:1132–34.
72. Jingushi, S., et al. (1991), "Biological cascades of fracture healing as modules for bone-biomaterial interfacial reactions," *The Bone-Biomaterial Interface*, Ed. Davies, J. E., University of Toronto Press, Toronto, 250–262.
73. Jones, H. C., et al., "Cement Disease," *Clin. Orth.* 225:192, 1987.
74. Juliano, R. L., et al. (1993), "Signal Transduction from the Extracellular Matrix," *Journal of Cell Biology* 120(3):577–585.
75. Kaelble, D. H. (1979), "Dispersion-Polar Surface Tension Properties of Organic Solids," Journal of Adhesion 2:66–81.
76. Kaelble, D. H., et al. (1974), "Interfacial Bonding and Environmental Stability of Polymer Matrix Composites," *Journal of Adhesion* 6:23–48.
77. Kallos, T., et al. "Intramedullary pressure and pulmonary embolization of femoral medullary contents in dogs during insertion of bone cement and a prosthesis," *JBJS* 56; 1363, 1974.
78. Kim, H. D., et al. (1997), "Human Osteoblast Response in vitro to PDGF and TGF-β Delivered from Controlled Release Polymer Rods," *Biomaterials* (in press).
79. Lane, T. F., et al. (1992), "Regulation of Gene Expression by SPARC during Angiogenesis in vitro: Changes in Fibronectin, Thrombospondin-1, and Plasminogen Activator-Inhibitor-1," *Journal of Biol. Chem.* 267(23):16736–16745.
80. Lane, T. F., et al. (1994), "SPARC is a source of copper-binding peptides that stimulate angiogenesis," *J. Cell Biol.* 125(4):929–43.
81. Langer, R., et al. (1990), "Future directions in biomaterials," *Biomaterials* 11:738–744.
82. Langer, R., et al. (1993), "Tissue Engineering," *Science* 260:920–926.
83. Lian, J., et al. (1989), "Structure of the rat osteocalcin gene and regulation of vitamin D-dependent expression," *PNAS* 86:1143–1147.
84. Lin, H., et al. (1994), "Synthesis, surface, and cell-adhesion properties of polyurethanes containing covalently grafter RGD-peptides," *Journal of Biomedical Materials Research* 28:329–342.
85. Lynch, M. P., et al. (1995), "The Influence of Type I Collagen on the Development and Maintenance of the Osteoblast Phenotype in Primary and Passaged Rat Calvarial Osteoblasts: Modification of Expression of Genes Supporting Cell Growth, Adhesion, and Extracellular Matrix Mineralization," *Experimental Cell Research* 216:35–45.
86. Makohliso, S. A, et la. (1993), "The magnitude and polarity of a fluoroethylene propylene electrode substrate charge influence neurite outgrowth in vitro," *J. Biomed. Mater. Res.* 27(8):1075–85.
87. Maquart, F. X., et al. (1993), "In vivo stimulation of connective tissue accumulation by the tripeptide-copper complex glycyl-L-histidyl-L-lysine-Cu2+ in rat experimental wounds," *J. Clin. Invest.* 92(5):2368–76.
88. Massia, S. P., et al. (1990a), "Covalent surface immobilization of Arg-Gly-Asp and Tyr-Ile-Gly-Ser-Arg-containing peptides to obtain well-defined cell-adhesive substrates," *Anal. Biochem.* 187:292–301.
89. Massia, S. P., et al. (1990b), "Covalently attached GRGD on polymer surfaces promotes biospecific adhesion of mammalian cells," *Annals of the New York Academy of Sciences* 589:261.
90. Matsuda, T., et al. (1987), "The in vitro response of osteoblasts to bioactive glass," *Biomaterials* 8:275–284.
91. Meredith, J. E., et al. (1996), "The Regulation of Growth and Intracellular Signalling by Integrins," *Endocrine Reviews* 17(3):207–213.
92. Morgan, H., et al. (1992), "A surface plasmon resonance immunosensor based on the streptavidin-biotin complex," *Biosensors and Bioelectronics* 7:405–410.
93. Newens, A. F., et al., "Severe hypotension during prosthetic hip surgery with acrylic bone cement Anesthes.," 36; 298, 1972.
94. Noda, M., et al. (1987), "cDNA cloning of alkaline phosphatase from rat-osteosarcoma (ROS 17/2.8) cells," *J. Bone Min. Res.* 2:161–164.
95. Oldberg, A., et al. (1988), "The primary structure of cell-binding salioprotein," *J. Biol. Chem* 263:19430–19432.
96. Oldberg, A., et al. (1986), "Cloning and sequence analysis of rat bone salioprotein (osteopontin) cDNA reveals an Arg-Gly-Asp cell-binding sequence," *Proc. Natl. Acad. Sci., USA* 83(23):8819–8823.
97. Patterson, R., et al. (1995), "Effects of radio frequency glow discharge and oligopeptides on the attachment of human endothelial cells to polyurethane," *ASAIO J.,* 41:234–252.
98. Peel, S. A. F., et al. (1992), "Polymer surface modification causes changes in phenotypic expression of primary bone cells," *Mat. Res. Soc. Symp. Proc.* 252:71–77.
99. Pesakova, V., et al. (1995), "Effect of the tripeptide glycyl-L-histidyl-L-lysine on the proliferation and synthetic activity of chick embryo chondrocytes," *Biomaterials* 16(12):911–915.
100. Pettit, L. D., et al. (1992), "The coordination of copper(II) to 1-hydroxy-4-(glycyl-histidyl-lysine)-anthraquinone; a synthetic model of anthraquinone anti-cancer drugs," *J Inorg. Biochem.* 45(3):203–210.
101. Pfaff, M., et al. (1994), "Selective recognition of cyclic RGD peptides of NMR defined conformation by aiibB3, aVB3, and a5B1 Integrins," *J. Biol. Chem.* 269(32):20233–20238.
102. Pierschbacher, M. D., et al. (1984), "Cell attachment activity of fibronectin can be duplicated by small synthetic fragments of the molecule," *Nature* 309:30–33.
103. Pierschbacher, M. D., et al. (1987), "Influence of Stereochemistry of the Sequence of Arg-Gly-Asp-Xaa on Binding Specificity in Cell Adhesion," *Journal of Biological Chemistry* 262(36):17294–17298.
104. Pilliar, R. M. (1987), "Porous-surface metallic implants for orthopaedic applications," *J. Biomed. Meter. Res.* 21(A1 Suppl):1–33.
105. Pistone, M., et al. (1996), "Integrin synthesis and utilization in cultured human osteoblasts," *Cell Biology International* 20(7):471–479.
106. Pohunkova, H., et al. (1995), "Reactivity and the fate of some composite bioimplants based on collagen in connective tissue," *Biomaterials* 16(1):67–71.
107. Prime, K. L., et al. (1991), "Self-Assembled Organic Monolayers: Model Systems for Studying Adsorption of Proteins at Surfaces," *Science* 252:1164–1167.
108. Puleo, D. A. (1994), "Activity of covalently immobilized enzyme on silanized Co—Cr—Mo," In: 19*th Annual Meeting of the Society for Biomaterials.*
109. Puelo, D. A. (1996), "Biochemical surface modification of Co—Cr—Mo," *Biomaterials* 17:217–222.

110. Puelo, D. A., et al. (1992), "Formation of focal contacts by osteoblasts on orthopedic biomaterials," *J. of Biomedical Research* 26:291–301.
111. Puelo, D. A., et al. (1991), "RGDS Tetrapeptide Binds to Osteoblasts and Inhibits Fibronectin-Mediated Adhesion," *Bone* 12:271–276.
112. Pytela, R., et al. (1987), "Arginine-glycine-aspartic acid adhesion receptors," *Methods in Enzymology* 144:475–489.
113. Ranieri, J. P., et al. (1995), "Neuronal cell attachment to fluorinated ethylene propylene films with covalently immobilized laminin oligopeptides YIGSR and IKVAV II," *Journal of Biomedical Research* 29: 779–785.
114. Ratner, B. D. (ed.) (1988), *Surface Characterization of Biomaterials*, Elsevier Science Publishing Company; New York, N.Y.
115. Robey, P. G., et al. (1993), "Structure and molecular regulation of bone matrix protein," *J. Bone Min. Res.* 2:S483–7.
116. Roskelley, C. D., et al. (1994), "Extracellular matrix-dependent tissue-specific gene expression in mammary epithelial cells requires both physical and biochemical signal transduction," *Proc. Natl. Acad. Sci., USA* 91:12378–12382.
117. Ruoslahti, E., et al. (1987), "New Perspectives in cell adhesion: RGD and integrins," *Science* 238:491–97.
118. Saito, T., et al., (1994), "Identification of integrin receptors on cultured human bone cells," *J. Orthopaedic Research* 12(3):384–394.
119. Sandberg, M. M., et al. (1993), "Gene expression during bone repair," *Clinical Orthopaedics and Related Research* 289:292–312.
120. Schaller, M. D. (1996), "The focal adhesion kinase," *Journal of Endocrinology* 150:1–7.
121. Schneider, G., et al. (1994), "Formation of Focal Adhesions by Osteoblasts Adhering to Different Substrata," *Experimental Cell Research* 214:264–269.
122. Stephel, G. C., et al. (1989), "Laminin. A chain synthetic peptide which supports neurite outgrowth," *Biochemical and Biophysical Research Communications* 162(2):821–829.
123. Sinnghvi, R., et al. (1994), "Engineering Cell Shape and Function," *Science* 264:696–698.
124. Soballe, K., et al., "Tissue ingrowth into titan and hydroxyapatite-coated implants during stable and unstable mechanical conditions," *J. Orthop. Res.*, 10; 2–299, 1992.
125. Spector, M. (1987), "Historical review of porous-coated implants," *J. Arthroplasty* 2:163–77.
126. Spector, M., et al., "Advances in our understand of the implant bone interface: factors affecting formation and degeneration. In Instructional Course Lectures, The American Academy of Orthopaedics, 40; 101–113, 1991.
127. Staatz, W. D., et al. (1991), "Identification of a tetrapeptide recognition sequence for the alpha-2, beta-1 integrin in collagen," *Journal of Biological Chemistry* 266:7363–7367.
128. Takatsuka, M. (1992), "Preparation of an RGD ALB conjugate. In vitro analysis of cellular responses," *ASAIO-J* 38(3):M275–8.
129. Takeuchi, Y., et al. (1996), "Differentiation and cell surface expression of transforming growth factor-beta receptors are regulated by interaction with matrix collagen in murine osteoblastic cells," *J. Biol. Chem.* 271(7):3938–44.
130. Tenenbaum, H. C., et al. (1982), "Differentiation of Osteoblasts and Formation of Mineralized Bone in vitro," *Calcif. Tissue Int.* 34:76–29.
131. Tisdel, C. L., et al., "The Influence of a hydroxyapatite and tricalcium phosphate coating on bone growth into titanium fiber-metal implants," *J. Bone Joint Sur.* 76A: 159, 1994.
132. Valentini, R. F., et al. (1997), "Increased Bone Formation and Pull-Out Strength with RGD-Coated vs. Uncoated Implants," *Soc. Biomaterials Abstracts* in press.
133. Valentini, R. F., et al. (1992), "Electrically charged polymeric substrates enhance nerve fiber outgrowth in vitro," *Biomaterials* 13:183–90.
134. Valentini, R. F., et al. (1993), "Patterned neuronal attachment and outgrowth on surface modified, electrically charged fluoropolymer substrates," *J. Biomater. Sci. Polymer Edn.* 5:13–36.
135. Valentini, R. F., et al. (1994), "Enhanced osteoblast attachment to amine- and RGD-immobilized fluoropolymer substrates," *Ortho. Res. Soc. Abstracts* 40.
136. Valentini, R. F., et al. (1997), "Increased and Differential Gene Expression of Cultured Osteoblasts to RGD- and RGE-Containing Peptides," *Ortho. Res. Soc. Abstracts* in press.
137. Valentini, R. F., et al. (1995), "Increased osteocalcin synthesis by rat calvarial osteoblasts on RGI grafted substrates," *Soc. Biomaterials Abstracts* 21:65.
138. van Dijk, et al. (1993), "Evidence that a non-RGD domain in rat osteopontin is involved in cell attachment," *Langmuir* 8:130–138.
139. Journal of Cell Biology 121: 461–468.
140. Vukicevic, S., et al. (1990), "Differentiation of canalicular cell processes in bone cells by basement membrane matrix components: regulation by discrete domains of laminin," *Cell* 63:437–45.
141. Vuori, K., et al. (1994), "Association of Insulin Receptor Substrate-1 with Integrins," *Science* 266:1576–1578.
142. Walsh, W. R., et al. (1995), "Controlled release of platelet-derived growth factor using ethylene vinyl acetate copolymer (EVAc) coated on stainless steel wires," *Biomaterials* 16:1319–1325.
143. Wang, N., et al. (1993), Mechanotransduction across the cell surface and through the cytoskeleton," *Science* 260:1124–27.
144. Whitesides, G. M., et al., "Molecular Self-Assembly and Nanochemistry: A Chemical Strategy for the Synthesis of Nanostructures," *Science* 254:1312–1319.
145. Wu, J. E., et al. (1994), "Complex patterns of expression suggest extensive roles for the alpha 2 beta 1 integrin in murine development," *Dev. Dyn.* 199(4):292–314.
146. Yasuda, T., et al. (1996), "Possible Involvement of RGD (Arg-Gly-Asp)-Containing Extracellular Matrix Proteins in Rat Growth Plate Chondrocyte Differentiation in Culture," *Journal of Bone and Mineral Research* 11(10):1430–1437.
147. Zhang, Z., et al. (1995), "The $_5$1 integrin supports survival of cells on fibronectin and up-regulates Bcl2 expression," *Proc. Natl. Acad. Sci. USA* 92:6161–6165.

Each of the foregoing patents, patent applications and references is herein incorporated by reference in its entirety. Having described the presently preferred embodiments in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

What I claim is:

1. A prosthetic device, comprising:
   a shaped substrate having a substrate surface, for implantation in a mammal;
   a layer of gold attached to the substrate surface and defining a tissue contacting surface; wherein the gold layer has a thickness of about 10 to 1000 Angstroms and,
   a bioactive peptide bound to the gold layer.

2. The device as in claim 1, wherein the bioactive peptide is selected from the group consisting of a cell modulating peptide, a chemotactic peptide, anticoagulant peptide, anti-thrombotic peptide, an anti-tumor peptide, an anti-infectious peptide, a growth potentiating peptide, and an anti-inflammatory peptide.

3. The device as in claim 2, wherein the cell modulating peptide is selected from the group consisting of an anti-integrin antibody fragment, a cadherin binding peptide, and an integrin binding peptide.

4. The device as in claim 3, wherein the cell modulating peptide is an integrin binding peptide which is selected from the group consisting of RGDC, RGEC, RGDT, DGEA, DGEAGC, EPRGDNYR, RGDS, EILDV, REDV, YIGSR, SIKVAV, RGD, RGDV, HRNRKGV, KKGHV, XPQPNPSPASPVVVGGGASLPEFXY, and ASPVVVGG-GASLPEFX.

5. A prosthetic device, comprising:
   a shaped substrate having a substrate surface, for implantation in a mammal;
   a layer of gold attached to the substrate surface and defining a tissue contacting surface; and, a bioactive peptide bound to the gold layer wherein the bioactive peptide is a chemotactic peptide and, wherein the chemotactic peptide is selected from the group consisting of functionally active fragments of collagen, fibronectin, laminin, and proteoglycan.

6. A prosthetic device, comprising:
   a shaped substrate having a substrate surface, for implantation in a mammal;
   a layer of gold attached to the substrate surface and defining a tissue contacting surface; and, a bioactive peptide bound to the gold layer, wherein the bioactive peptide is an anti-tumor peptide and, wherein the anti-tumor peptide is selected from the group consisting of functionally active fragments of protein anti-tumor molecules.

7. The device as in claim 2, wherein the anti-infectious peptide is selected from the group consisting of functionally active fragments of the protein anti-infectious molecules.

8. A prosthetic device, comprising:
   a shaped substrate having a substrate surface, for implantation in a mammal;
   a layer of gold attached to the substrate surface and defining a tissue contacting surface; and, a bioactive peptide bound to the gold layer, wherein the bioactive peptide is a growth potentiating peptide and, wherein the growth potentiating peptide is selected from the group consisting of functionally active fragments of PDGF, EGF, FGF, TGF, NGF, CNTF, GDNF, and type I collagen peptides.

9. The device as in claim 2, wherein the anti-inflammatory peptide is selected from the group consisting of functionally active fragments of anti-inflammatory molecules.

10. The device as in claim 1, wherein the layer of gold is attached to the substrate surface via attachment to a layer of titanium intermediate the gold layer and the substrate surface.

11. The device as in claim 1, wherein the shaped substrate is selected from the group consisting of a polymer, a metal, a plastic, a fabric, a ceramic, a biological material, and a composite of two or more materials.

12. A prosthetic device, comprising:
    a shaped substrate having a substrate surface, for implantation in a mammal;
    a layer of gold attached to the substrate surface and defining a tissue contacting surface; and, a bioactive peptide bound to the gold layer, wherein the bioactive peptide forms a layer about 1 to 500 Angstroms in thickness.

13. The device as in claim 1, wherein at least two bioactive peptides are bound to the surface.

14. A prosthetic device, comprising:
    a shaped substrate having a substrate surface, for implantation in a mammal;
    a layer of gold attached to the substrate surface and defining a tissue contacting surface; and, a bioactive peptide bound to the gold layer, wherein the bioactive molecule is bound to the gold by a gold-sulfide bond.

15. A prosthetic device, comprising:
    a shaped substrate formed of a textured material having a substrate surface with first projections and first indentations; and
    a layer of gold attached to the substrate surface of the textured material, wherein the layer of gold creates a gold surface that has second projections said second indentations corresponding to said first projections and indentations.

16. The device as in claim 15, wherein the layer of gold has an approximately uniform thickness across the substrate of the textured material.

17. The device as in claim 15, wherein the textured material is a polymer.

18. The device as in claim 15, wherein the gold layer has a thickness of about 10 to 1000 Angstroms.

19. The device as in claim 15, further comprising a layer of bioactive peptide attached to the gold surface through a gold-sulfide bond.

20. A prosthetic device, comprising:
    a shaped substrate having a substrate surface;
    a layer of gold attached to the substrate surface; and
    an RGDC peptide attached to the gold layer through a gold-sulfide bond, wherein the RGDC peptide forms a layer about 1 to 500 Angstroms in thickness.

21. The device as in claim 20, wherein the layer of gold is attached to the substrate surface via attachment to a layer of titanium intermediate the gold layer and the substrate surface.

22. The device as in claim 20, wherein the shaped substrate is selected from the group consisting of a polymer, a metal, a plastic, a fabric, a ceramic, a biological material, and a composite of two or more materials.

23. A prosthetic device, comprising:
    a shaped substrate having a substrate surface;
    a layer of gold attached to the substrate surface; and
    an RGDC peptide attached to the gold layer through a gold-sulfide bond, wherein the gold layer has a thickness of about 10 to 1000 Angstroms.

24. A prosthetic device, comprising:
    a shaped substrate having a substrate surface;
    a layer of gold attached to the substrate surface; and
    an RGDC peptide attached to the gold layer through a gold-sulfide bond, wherein the surface of the prosthetic device is formed of a porous material and wherein the layer of gold creates a gold surface that has projections and indentations and wherein the layer of gold has an approximately uniform thickness across the surface of the porous material.

25. A prosthetic device, comprising:

a shaped substrate having a substrate surface, for implantation in a mammal;

a layer of gold attached to the substrate surface and defining a tissue contacting surface; and, a bioactive molecule bound to the gold layer, wherein the bioactive molecule is selected from the group consisting of a cell modulating molecule, a chemotactic molecule, anticoagulant molecule, antithrombotic molecule, an anti-tumor molecule, an anti-infectious molecule, a growth potentiating molecule, and an anti-inflammatory molecule.

26. The device as in claim 25, wherein the cell modulating molecule is selected from the group consisting of an antibody, a bone morphogenic protein, an integrin binding protein, and a cadherin binding protein.

27. The device as in claim 26, wherein the cell modulating molecule is a bone morphogenic protein.

28. The device as in claim 25, wherein the chemotactic molecule is selected from the group consisting of collagen, fibronectin, laminin, and proetoglycan.

29. The device as in claim 25, wherein the anti-tumor molecule is selected from the group consisting of methotrexate, adriamycin, cyclophosphamide, and taxol.

30. The device as in claim 25, wherein the anti-infectious molecule is selected from the group consisting of antibiotics such as penicillin.

31. The device as in claim 25, wherein the growth potentiating molecule is selected from the group consisting of PDGF, EGF, FGF, TGF, NGF, CNTF, and GDNF.

32. The device as in claim 25, wherein the anti-inflammatory molecule is selected from the group consisting of steroidal and non-steroidal compounds.

33. The device as in claim 25, wherein the layer of gold is attached to the substrate surface via attachment to a layer of titanium intermediate the gold layer and the substrate surface.

34. The device as in claim 25, wherein the shaped substrate is selected from the group consisting of a polymer, a metal, a plastic, a fabric, a ceramic, a biological material, and a composite of two or more materials.

35. A prosthetic device, comprising:

a shaped substrate having a substrate surface, for implantation in a mammal;

a layer of gold attached to the substrate surface and defining a tissue contacting surface; and, a bioactive molecule bound to the gold layer, wherein the gold layer has a thickness of about 10 to 1000 Angstroms.

36. A prosthetic device, comprising:

a shaped substrate having a substrate surface, for implantation in a mammal;

a layer of gold attached to the substrate surface and defining a tissue contacting surface; and, a bioactive molecule bound to the gold layer, wherein the bioactive molecule forms a layer about 1 to 500 Angstroms in thickness.

37. A prosthetic device, comprising:

a shaped substrate having a substrate surface, for implantation in a mammal;

a layer of gold attached to the substrate surface and defining a tissue contacting surface; and, a bioactive molecule bound to the gold layer, wherein the surface of the prosthetic device is formed of a porous material and wherein the layer of gold creates a gold surface that has projections and indentations said corresponding to the projections and indentations.

38. The device as in claim 37, wherein the layer of gold has an approximately uniform thickness across the surface of the porous material.

39. The device as in claim 37, wherein at least two bioactive peptides are bound to the surface.

* * * * *